(12) United States Patent
Genin et al.

(10) Patent No.: US 6,387,896 B1
(45) Date of Patent: May 14, 2002

(54) BICYCLIC OXAZOLIDINONES AS ANTIBACTERIAL AGENTS

(75) Inventors: Michael J. Genin, Paw Paw; Michael Robert Barbachyn, Kalamazoo; Jackson B. Hester, Jr., Galesburg; Paul D. Johnson, Kalamazoo, all of MI (US)

(73) Assignee: Pharmacia & Upjohn Co., Kalamazoo, MI (US)

( * ) Notice: Subject to any disclaimer, the term of this patent is extended or adjusted under 35 U.S.C. 154(b) by 0 days.

(21) Appl. No.: 09/572,167

(22) Filed: May 17, 2000

Related U.S. Application Data

(60) Provisional application No. 60/136,250, filed on May 27, 1999.

(51) Int. Cl.[7] .................. A61K 31/54; A61K 31/535; C07D 263/00; C07D 215/00; A61P 31/04
(52) U.S. Cl. .................. 514/230.5; 514/224.2; 514/249; 514/314; 514/376; 544/58.4; 544/58.7; 544/105; 544/353; 546/165; 546/166; 548/231; 548/232
(58) Field of Search .............. 514/224.2, 230.5, 514/249, 314, 376; 544/58.4, 58.7, 105, 353; 546/165, 166; 548/231, 232

(56) References Cited

U.S. PATENT DOCUMENTS

| | | | |
|---|---|---|---|
| 4,965,268 A | 10/1990 | Wang et al. | 514/253 |
| 5,032,605 A | 7/1991 | Wang et al. | 514/376 |
| 5,036,092 A | 7/1991 | Wang et al. | 514/376 |
| 5,036,093 A | 7/1991 | Wang et al. | 514/376 |
| 5,039,690 A | 8/1991 | Wang et al. | 514/376 |
| 5,164,510 A | 11/1992 | Brickner | 548/231 |
| 5,684,023 A | 11/1997 | Riedl et al. | 514/376 |
| 5,792,765 A | 8/1998 | Riedl et al. | 514/236.8 |

FOREIGN PATENT DOCUMENTS

| | | |
|---|---|---|
| EP | 0 127 902 A2 | 6/1984 |
| EP | 0 311 090 A1 | 12/1989 |
| EP | 0 694 544 A1 | 1/1996 |
| EP | 0 789 025 A1 | 8/1997 |
| WO | WO90/02744 | 3/1990 |
| WO | WO97/19089 | 5/1997 |
| WO | WO99/37641 | 7/1999 |

OTHER PUBLICATIONS

J. Med. Chem. 1992, 35, 1156–1165—Antibacterials. Synthesis and Structure — Activity Studies of 3–Aryl–2–oxooxazolidines. 4. Multiply–Substituted Aryl Derivatives.

*Primary Examiner*—Brenda Coleman
(74) *Attorney, Agent, or Firm*—Lucy X. Yang; Jonathan P. O'Brien

(57) ABSTRACT

The present invention provides compounds of formula I useful as antimicrobial agents

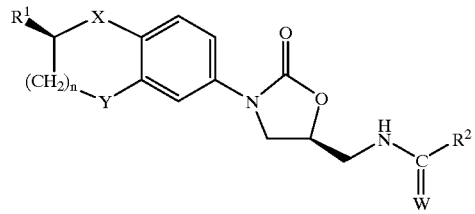

wherein W, X, Y, $R^1$, $R^2$ and n are as defined in thereof.

21 Claims, No Drawings

BICYCLIC OXAZOLIDINONES AS ANTIBACTERIAL AGENTS

This application claims the benefit of U.S. Provisional Application No. 60/136,250 filed May 27, 1999.

FIELD OF THE INVENTION

The present invention relates to novel bicyclic oxazolidinone compounds and their preparations, more specifically, to $R^1$-substituted bicyclic oxazolidinones as shown in formula I. These compounds have potent activities against gram positive and gram-negative bacteria.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium*.

However, oxazolidinones generally do not demostrate an activity at a useful level against aerobic gram-negative organisms. Thus, the use of these oxazolidinone antibacterial agents is limited to infectious states due to gram-positive bacteria. Accordingly, it is among the objects of the present invention to provide pharmaceutical compounds which have broader antibacterial activity including the activity against aerobic gram-negative organisms. We have now discovered that the incorporation of a $R^1$ group at the bicyclic oxazolidinone imparts an unexpected increase in antibacterial activity as well as in the spectrum of activity to include gram-negative organisms such as *Haemophilus influenza* and *Moraxella catarrhalis*. More importantly, this increase in the potency and spectrum of activity is only seen in the specified diastereomers of formula I.

INFORMATION DISCLOSURE

U.S. Pat. No. 5,164,510 discloses 5'-indolinyloxazolidin-2-ones of formula XI

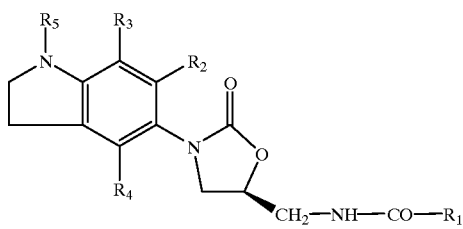

which are useful as antibacterial agents.

U.S. Pat. Nos. 5,036,092; 5,036,093; 5,039,690; 5,032,605 and 4,965,268 disclose aminomethyl oxazolidinyl aza cycloalkylbenzene derivatives useful as antibacterial agents.

U.S. Pat. Nos. 5,792,765 and 5,684,023 disclose substituted oxazolidinones useful as antibacterial agents.

SUMMARY OF THE INVENTION

The present invention provides a compound of formula I

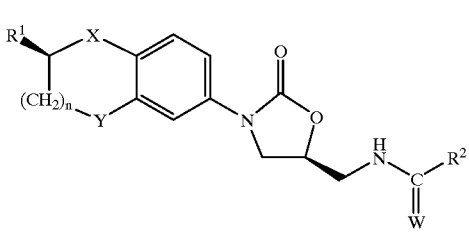

or a pharmaceutically acceptable salt thereof wherein

W is
a) O, or
b) S;

X is
a) —S(=O)$_m$—, or
b) —NR$^3$—;

Y is
a) —O—,
b) —NH—,
c) —CH$_2$—, or
d) —S(=O)$_m$—;

$R^1$ is C$_{1-4}$ alkyl, optionally substituted with 1–3 $R^5$;

$R^2$ is
a) H,
b) C$_{1-6}$ alkyl, optionally substituted with 1–3 halo;
c) cyclopropyl,
d) —OC$_{1-4}$ alkyl,
e) —NH$_2$,
f) —NHC$_{1-6}$ alkyl, or
g) —N(C$_{1-6}$ alkyl)$_2$;

$R^3$ is
a) C$_{1-8}$ alkyl, optionally substituted with 1–3 halo, CN, NO$_2$, OH, SH or NH$_2$,
b) —C(=O)R$^4$, or
c) —C(=S)NHC$_{1-4}$ alkyl;

$R^4$ is
a) H,
b) C$_{1-6}$ alkyl, optionally substituted with OH, C$_{1-4}$ alkoxy, NH$_2$, SH or halo, or
c) —CH$_2$OC(=O)C$_{1-4}$ alkyl;

$R^5$ is
a) halo,
b) —CN,
c) —OH,
d) —SH,
e) —NH$_2$,
f) —OR$^6$,
g) —NHR$^6$,
h) —N(R$^6$)$_2$, or
i) —S(=O)$_m$R$^6$;

$R^6$ is
a) C$_{1-6}$ alkyl,
b) —C(=O)C$_{1-4}$ alkyl,
c) —C(=O)OC$_{1-4}$ alkyl,
d) —C(=O)NH$_2$,
e) —C(=O)NHC$_{1-4}$ alkyl, or
f) —SO$_2$C$_{1-4}$ alkyl;

m is 0, 1 or 2;

n is 0 or 1;

with the proviso that where n is 0, Y is —CH$_2$—.

In another aspect, the present invention also provides:

a pharmaceutical composition comprising a compound of formula I, or a pharmaceutically acceptable salt thereof, and a pharmaceutically acceptable excipient (the composition preferably comprises a therapeutically effective amount of the compound or salt), a method for treating gram-positive microbial infections in humans or other warm-blooded animals by administering to the subject in need a therapeutically effective amount of a compound of formula I, or a pharmaceutically acceptable salt thereof, a method for treating gram-negative microbial infections in humans or other warm-blooded animals by administering to the subject in need a therapeutically effective amount of a compound of formula I, or a pharmaceutically acceptable salt thereof.

The invention also provides some novel intermediates and processes disclosed herein that are useful for preparing compounds of formula I.

DETAILED DESCRIPTION OF THE INVENTION

The following definitions are used, unless otherwise described.

The term halo refers to fluoro, chloro, bromo, or iodo.

The term alkyl, alkoxy, etc. refer to both straight and branched groups, but reference to an individual radical such as "propyl" embraces only the straight chain radical, a branched chain isomer such as "isopropyl" being specifically referred to.

The carbon atom content of various hydrocarbon-containing moieties is indicated by a prefix designating the minimum and maximum number of carbon atoms in the moiety, i.e., the prefix $C_{i\text{-}j}$ indicates a moiety of the integer "i" to the integer "j" carbon atoms, inclusive. Thus, for example, $C_{1\text{-}7}$ alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

It will be appreciated by those skilled in the art that compounds of the present may have additional chiral centers and be isolated in optically active or racemic form. The present invention encompasses any racemic, optically-active (such as enantiomers, diastereomers), tautomeric, or stereoisomeric form, or mixture thereof, of a compound of the invention.

Specific and preferred values listed below for radicals, substituents, and ranges, are for illustration only; they do not exclude other defined values or other values within defined ranges for the radicals and substituents.

Specifically, $C_{1\text{-}4}$ alkyl, $C_{1\text{-}6}$ alkyl and $C_{1\text{-}8}$ alkyl can be an alkyl group having one to four, one to six, or one to eight carbon atoms respectively such as, for example, methyl, ethyl, propyl, butyl, pentyl, hexyl, heptyl, octyl and their isomeric forms thereof; $C_{1\text{-}4}$ alkoxy can be an alkyl group having one to four carbon atoms attached to an oxygen atom of hydroxyl group such as, for example, methoxy, ethoxy, propyloxy, butyloxy and their isomeric forms thereof.

A preferred value for halo is fluoro or chloro.

A preferred value for W is sulfur atom.

A preferred value for X is —$NR^3$— wherein $R^3$ is as defined above.

A preferred value for Y is —$CH_2$— or oxygen atom.

A preferred value for $R^1$ is methyl or methyl substituted with fluoro.

A more preferred value for $R^1$ is methyl.

A specific value for $R^2$ is $C_{1\text{-}6}$ alkyl, $C_{1\text{-}6}$ alkyl substituted with 1–3 halo, $NH_2$, $NHC_{1\text{-}6}$ alkyl, or $N(C_{1\text{-}6}$ alkyl$)_2$;

A preferred value for $R^2$ is methyl, ethyl, dichloromethyl, dichloroethyl, or $NH_2$.

A more preferred value for $R^2$ is methyl and ethyl.

A specific value for $R^3$ is $C_{1\text{-}8}$ alkyl, $C_{1\text{-}8}$ alkyl substituted with 1–3 halo, CN, $NO_2$, OH, SH or $NH_2$, C(=S)$NHC_{1\text{-}4}$ alkyl, or C(=O)$R^4$ wherein specific value for $R^4$ is H, $C_{1\text{-}6}$ alkyl, optionally substituted with OH, $C_{1\text{-}4}$ alkoxy, $NH_2$, SH or halo, or $CH_2$ OC(=O)$C_{1\text{-}4}$ alkyl.

A preferred value for $R^3$ is 2-fluoroethyl, glycolyl, formyl, methoxyacetyl, oxoethylacetate, acetyl, or methylaminocarbothioyl.

A more preferred value for $R^3$ is formyl or acetyl.

A specific value for $R^5$ is halo, —CN, —OH, —SH, —$NH_2$, —$OR^6$, —$NHR^6$, —$N(R^6)_2$, or —S(=O)$R^6$.

A specific value for $R^6$ is $C_{1\text{-}6}$ alkyl, —C(=O)$C_{1\text{-}4}$ alkyl, —C(=O)$OC_{1\text{-}4}$ alkyl, —C(=O)$NH_2$, —C(=O)$NHC_{1\text{-}4}$ alkyl, or —$SO_2C_{1\text{-}4}$ alkyl.

Examples of the present invention are:

a) N-({(5S)-3-[(2R)-1-(2-fluoroethyl)-2-methyl-2,3-dihydro-1H-indol-5-yl]-2-oxo-1,3-oxazolidin-5-yl}methyl)acetamide;

b) N-{[(5S)-3-((2R)-1-glycoloyl-2-methyl-2,3-dihydro-1H-indol-5-yl)-2-oxo-1,3-oxazolidin-5-yl]methyl}acetamide;

c) N-({(5S)-3-[(2R)-1-glycoloyl-2-methyl-2,3-dihydro-1H-indol-5-yl]-2-oxo-1,3-oxazolidin-5-yl}methyl)acetamide;

d) N-({(5S)-3-[(2R)-1-formyl-2-methyl-2,3-dihydro-1H-indol-5-yl]-2-oxo-1,3-oxazolidin-5-yl}methyl)acetamide;

e) N-({(5S)-3-[(2R)-1-formyl-2-methyl-2,3-dihydro-1H-indol-5-yl]-2-oxo-1,3-oxazolidin-5-yl}methyl)propanamide;

f) N-({(5S)-3-[(2R)-1-formyl-2-methyl-2,3-dihydro-1H-indol-5-yl]-2-oxo-1,3-oxazolidin-5-yl}methyl)ethanethioamide;

g) N-({(5S)-3-[(2R)-1-(2-methoxyacetyl)-2-methyl-2,3-dihydro-1H-indol-5-yl]-2oxo-1,3-oxazolidin-5-yl}methyl)acetamide;

h) 2-((2R)-5-{(5S)-5-[(acetylamino)methyl]-2-oxo-1,3-oxazolidin-3-yl}-2-methyl-2,3-dihydro-1H-indol-1-yl)-2-oxoethyl acetate;

i) N-({(5S)-3-[(2R)-1-acetyl-2-methyl-2,3-dihydro-1H-indol-5-yl]-2-oxo-1,3-oxazolidin-5-yl}methyl)acetamide;

j) N-[((5S)-3-{(2R)-2-methyl-1-[(methylamino)carbothioyl]-2,3-dihydro-1H-indol-5-yl}-2-oxo-1,3-oxazolidin-5-yl)methyl]acetamide;

k) 2-((2R)-5-{(5S)-5-[(ethanethioylamino)methyl]-2-oxo-1,3-oxazolidin-3-yl}-2-methyl-2,3-dihydro-1H-indol-1-yl)-2-oxoethyl acetate;

l) N-({(5S)-3-[(2R)-1-glycoloyl-2-methyl-2,3-dihydro-1H-indol-5-yl]-2-oxo-1,3-oxazolidin-5-yl}methyl)ethanethioamide;

m) N-{[(5S)-3-[(2R)-1-formyl-2-methyl-1,2,3,4-tetrahydro-6-quinolinyl]-2-oxo-1,3-oxazolidin-5-yl]methyl}acetamide;

n) N-{[(5S)-3-[(2R)-1-glycoloyl-2-methyl-1,2,3,4-tetrahydro-6-quinolinyl]-2-oxo-1,3-oxazolidin-5-yl]methyl}acetamide;

o) N-({(5S)-3-[(2R)-1-formyl-2-methyl-1,2,3,4-tetrahydro-6-quinolinyl]-2-oxo-1,3-oxazolidin-5-yl}methyl)acetamide;

p) N-({(5S)-3-[(2R)-1-formyl-2-methyl-1,2,3,4-tetrahydro-6-quinolinyl]-2-oxo-1,3-oxazolidin-5-yl}methyl)ethanethioamide;

q) N-{[(5S)-3-[(3R)4-Formyl-3-methyl-3,4-dihydro-2H-1,4-benzoxazin-7-yl]-2-oxo-1,3-oxazolidin-5-yl]methyl}acetamide;

r) N-({(5S)-3-[(3R)-4-Formyl-3-methyl-3,4-dihydro-2H-1,4-benzoxazin-7-yl]-1,2-oxo-1,3-oxazolidin-5-yl}methyl)acetamide;

s) N-({(5S)-3[(3R)-4-Formyl-3-methyl-3,4-dihydro-2H-1,4-benzoxazin-7-yl]-2-oxo-1,3-oxazolidin-5-yl}methyl)ethanethioamide;

t) N-({(5S)-3-[(2R)2-(fluoromethyl)-1-formyl-2,3-dihydro-1H-indol-5-yl]-2-oxo-1,3-oxazolidin-5-yl}methyl)acetamide;

u) N-{[(5R)-3-(2(+)-methyl-2,3-dihydro-1-benzothien-5-yl)-2-oxo-1,3-oxazolidin-5-yl]methyl}acetamide; or v) N-[[(5S)-3-[2-(1,1-dimethylethyl)-1-formyl-2,3-dihydro-1H-indol-5-yl]-2-oxo-5-oxazolidinyl]methyl]ethanethioamide.

Preferred examples of the present invention are:

a) N-({(5S)-3-[(2R)-1-formyl-2-methyl-2,3-dihydro-1H-indol-5-yl]-2-oxo-1,3-oxazolidin-5-yl}methyl)ethanethioamide;

b) N-({(5S)-3-[(2R)-1-(2-methoxyacetyl)-2-methyl-2,3-dihydro-1H-indol-5-yl]-2-oxo-1,3-oxazolidin-5-yl}methyl)acetamide;

c) 2-((2R)-5-{(5S)-5-[(acetylamino)methyl]-2-oxo-1,3-oxazolidin-3-yl}-2-methyl-2,3-dihydro-1H-indol-1-yl)-2-oxoethyl acetate;

d) N-({(5S)-3-[(2R)-1-acetyl-2-methyl-2,3-dihydro-1H-indol-5-yl]-2-oxo-1,3-oxazolidin-5-yl}methyl)acetamide;

e) N-[((5S)-3-{(2R)-2-methyl-1-[(methylamino)carbothioyl]-2,3-dihydro-1H-indol-5-yl}-2-oxo-1,3-oxazolidin-5-yl)methyl]acetamide;

f) 2-((2R)-5-{(5S)-5-[(ethanethioylamino)methyl]-2-oxo-1,3-oxazolidin-3-yl}-2-methyl-2,3-dihydro-1H-indol-1-yl)-2-oxoethyl acetate;

g) N-({(5S)-3-[(2R)-1-glycoloyl-2-methyl-2,3-dihydro-1H-indol-5-yl]-2-oxo-1,3-oxazolidin-5-yl}methyl)ethanethioamide;

h) N-({(5S)-3-[(2R)-1-formyl-2-methyl-1,2,3,4-tetrahydro-6-quinolinyl]-2-oxo-1,3-oxazolidin-5-yl}methyl)acetamide;

i) N-({(5S)-3-[(2R)-1-formyl-2-methyl-1,2,3,4-tetrahydro-6-quinolinyl]-2-oxo-1,3-oxazolidin-5-yl}methyl)ethanethioamide;

j) N-({(5S)-3-[(3R)4-Formyl-3-methyl-3,4-dihydro-2H-1,4-benzoxazin-7-yl]-2-oxo-1,3-oxazolidin-5-yl}methyl)acetamide;

k) N-({(5S)-3-[(3R)-4-Formyl-3-methyl-3,4-dihydro-2H-1,4-benzoxazin-7-yl]-2-oxo-1,3-oxazolidin-5-yl}methyl)ethanethioamide; or l) N-[[(5S)-3-[2-(1,1-dimethylethyl)-1-formyl-2,3-dihydro-1H-indol-5-yl]-2-oxo-5-oxazolidinyl]methyl]ethanethioamide.

More preferred examples of the present invention are:

a) N-({(5S)-3-[(2R)-1-formyl-2-methyl-2,3-dihydro-1H-indol-5-yl]-2-oxo-1,3-oxazolidin-5-yl}methyl)ethanethioamide;

b) N-({(5S)-3-[(2R)-1-glycoloyl-2-methyl-2,3-dihydro-1H-indol-5-yl]-2-oxo-1,3-oxazolidin-5-yl}methyl)ethanethioamide;

c) N-({(5S)-3-[(2R)-1-formyl-2-methyl-1,2,3,4-tetrahydro-6-quinolinyl]-2-oxo-1,3-oxazolidin-5-yl}methyl)ethanethioamide; or d) N-({(5S)-3-[(3R)-4-Formyl-3-methyl-3,4-dihydro-2H-1,4-benzoxazin-7-yl]-2-oxo-1,3-oxazolidin-5-yl}methyl)ethanethioamide.

The following Schemes describe the preparation of compounds of the present invention. All of the starting materials are prepared by procedures described in these schemes or by procedures that would be well known to one of ordinary skill in organic chemistry. The variables used in the Schemes are as defined below or as in the claims. The compounds of this invention can be prepared in accordance to one or more of the processes discussed below.

Indolines

As shown in Chart I, 2-alkylindolines can be prepared from known compound indole 1. Boc-protection of the indole nitrogen using di-t-butyldicarbonate and catalytic DMAP followed by regioselective metalation with n-butyllithium, sec-butyllithium or tert-butyllithium and alkylation with an appropriate electrophile such as alkyl bromides and iodides gives N-Boc-2-alkylindoles 3 (R is an alkyl or a electrophile group). Removal of the boc-protecting group affords 2-alkylindoles 4 which can be nitrated with $NaNO_3$ in sulfuric acid to give 2-alkyl-5-nitroindoles 5. Structure 5 is then reacted with sodium cyanoborohydride to give reduction product, the racemic indolines 6. The nitro group can then be reduced by catalytic hydrogenation in the presence of a suitable catalyst, such as palladium on carbon in a suitable solvent such as ethylacetate, THF, methanol or combinations thereof to afford the 2-alkyl-5-aminoindolines 7 as racemic mixtures. Treatment of 7 with benzyl chloroformate (2 equivalents) in THF with an appropriate base, such as sodium bicarbonate, potassium carbonate or triethylamine gives the bis-Cbz-protected materials of general structure 8. Alternatively, the intermediate R,S-2-alkylnitroindolines can be separated via chiral HPLC to afford enentiomerically pure R- and S-2-alkyl-5-nitroindolines 9 and 10. These materials can then be taken on separately in a chiral synthesis of the desired analogs.

In addition, where other groups besides alkyl are desired at the 2-position of the indoline, one can start with the known ethyl 5-nitroindole-2-carboxylate 11 (Chart II). Reduction of the nitro group to ethyl 5-aminoindole-2-carboxylate can be done via hydrogenation. Structure 12 then be reduced to the indoline intermediate 13 according to the procedure of Young et.al. (Tetrahedron Lett. 1986, 27, 2409–2410) with magnesium in methanol. Bis-protection of the nitrogens with the Cbz-group using benzyl chloroformate provides 14. Reduction of the ester to the alcohol 15 with an appropriate base such as LAH, $NaBH_4$ or DIBAL in a solvent such as diethyl ether or THF or methanol can then be done. Protection of the hydroxyl group with an appropriate protecting group (R') such as a silyl or benzyl ether provides 16.

The protected indolines thus prepared can be converted to the final oxazolidinone analogs as outlined in Chart III (R is H, an alkyl group or OR'; wherein R' is a protecting group). The carbamate derivatives 8, 16 and 18 can be deprotonated with a lithium base such as n-butyllithium, lithium diisopropylamide (LDA), or lithium bis(trimethylsilyl)amide (LHMDS) in a suitable solvent such as THF, N,N-dimethylformamide (DMF), or mixtures thereof, at a suitable temperature, typically in a range from −78° C. to −40° C. to give a lithiated intermediate which is directly treated with R-(−)-glycidyl butyrate. Warming to room temperature then affords (hydroxymethyl)oxazolidinones 19. In cases where racemic starting materials are used, compound 19 is obtained as a mixture of two diastereoisomers. In the event that enantiomerically pure intermediates are employed, compound 19 is obtained as one diastereomer. The diastereomeric mixtures of (hydroxymethyl)oxazolidinones 19 can be separated via chiral HPLC into single compounds and crystallized in an appropriate solvent such as $CHCl_3$, $Et_2O$, $CH_2Cl_2$, hexane, alcohol, ethyl acetate, THF, acetone or a mixture of them thereof to obtain x-ray structures to determine the absolute stereochemistry.

As shown in Chart III, the hydroxymethyl derivatives can be converted to the corresponding mesylate 20 (R'=Me) or nosylate 20 (R'=3-$NO_2$Ph) by treatment with methanesulfonyl chloride in the presence of triethylamine or pyridine, or meta-nitrophenylsulfonyl chloride in the presence of pyridine respectively. The resulting sulfonate 20 can be treated with an alkali metal azide, such as potassium or sodium azide in an aprotic solvent such as DMF, or N-methylpyrrolidinone (NMP) with an optional catalyst such as 18-crown-6 at a temperature in the range of 50–90° C. to afford azides 21. The azides can be reduced to the corresponding amine 22 by hyrdrogenation in the presence of a palladium, platinum or nickel catalyst, in an appropriate solvent such as THF, ethyl acetate, or methanol. Alternatively, azides 21 can be reduced to amines 22 by treatment with triphenylphosphine or other trivalent phosphorous compounds in a solvent such as THF, followed by addition of water and heating to temperatures up to 65° C. A more direct route to the amines 22 is to reflux the sulfonates 20 in isopropanol/THF/ammonium hydroxide under a dry ice/acetone condenser. The amines 22 thus obtained can be acylated by reactions well known to those skilled in the art to give (acylaminomethyl)oxazolidinones of structural formula 23. It can also be seen that other acyl derivatives, such as carbamates, can be prepared under similar conditions. Furthermore, treatment of intermediates 23 (W=O) with Lawesson's reagent in refluxing toluene or THF will afford thioamides 23 (W=S). The Cbz-group of the (acylaminomethyl)oxazolidinones 23 can be removed via hydrogenation in the presence of an appropriate catalyst such as palladium on carbon in solvents such as THF, methanol, ethyl acetate, dichloromethane or mixtures thereof to afford deprotected intermediates of general structure 24. Alternatively, solvolysis of Cbz-derivatives 23 in 40% HBr/acetic acid followed by removal of solvent provides deprotected intermediates 24 as hydrobromide salts. The deprotected materials can be acylated by reactions well known to those skilled in the art to give oxazolidinones of structural formula 25 ($R^3$=acyl). It can also be seen that other acyl derivatives, such as carbamates, can be prepared under similar conditions. In addition, the deprotected materials can be alkylated by reactions well known to those skilled in the ad to give oxazolidinones of structural formula 25 ($R^3$=alkyl).

Where other substitution on the 2-position of the indoline is desired, the protected alcohol derivatives 25 (R=OSi$R_3$, or OBn) can be deprotected with flouride in the case of the silyl ethers or catalytic hydrogenation in the case of the benzyl ethers. The resulting alcohols 26 can be alkylated to prepare other ether derivatives 27 (R'''=O-alkyl) or acylated to give esters 27 (R'''=O-acyl). Alternatively, they can be activated as sulfonates and displaced with nucleophiles to yield aminomethyl derivatives 27 (R'''=$NH_2$ or NHalkyl) which can be acylated, sulfonylated and/or alkylated to give 27 (R'''=NHCOH, NHCOalkyl, NHSO$_2$alkyl) by methods well known to those trained in the art. Finally, such alcohols may be converted to the fluoro derivative via treatment with (diethylamino)sulfur trifluoride.

Benzthiophenes

Chart IV ($R^1$ is as defined above and R' is a protecting group) shows the synthesis of 2-substituted-2,3-dihydro-1-benzothiophene intermediates 33 and 39. Aniline 29 can be prepared by reacting a known compound, methyl 5-nitro-1-benzothiophene-2-carboxylate 28 (Syn. Comm. 1991, 21, 959–964), with Raney nickel or stannous chloride in refluxing ethanol. Cbz-protection and reduction to the benzothiophene 31 can be obtained according to the method descried in Youn et.al. (Tetrahedron Lett. 1986, 27, 2409–2410) using magnesium in methanol. Following the procedure described in Chart II, ester 31 can be converted to the protected alcohol 33. If desired, the sulfur atom can be oxidized to the sulfoxide or sulfone at various stages in the synthesis by methods well known to those skilled in the art.

Alternatively, the requisite 2-substituted benzothiophenes can be prepared via thio-Claisen rearrangement of allyl aryl sulfoxides 37 (J.C.S. Chem. Comm. 1974, 850). The requisite allylic sulfides 36 can be prepared from a commercially available compound, 4-aminothiophenol, to give structure 35, via the protection of the aniline with benzyl chloroformate. The allylation of the sulfide with allylic halides provides 36 which can be oxidized to the sulfoxides 37 with a sodium periodate. Thermal rearrangement in an appropriate solvent such as dimethylaniline or DMF at temperatures ranging from 100–150° C. provides the desired intermediates 38. The sulfoxide can be mantained throughout the synthesis or it can be reduced to the sulfides 39 at this time via various methods such as using NaI and trifluoroacetic anhydride in acetone (J. Org. Chem 1994, 58, 3459–3466); or $BF_3$.$OEt_2$ and NaI in acetonitrile (Tetrahedron Asymmetry 1997, 8, 3503–3511); or triphenylphosphine and catalytic ReOCl$_3$(PPh$_3$)$_2$ in dichloromethane (Tetrahedron Lett. 1996, 7941–7944). The remaining steps which lead 33 and 39 to the desired oxazolidinone analogs of type 40a and 40b are similar to these described in Charts I–IV.

Dihydrobenzofurans

As shown in Chart V (wherein R is an alkyl group, R' is a protecting group, and $R^1$ is as defined above), 2,3-dihydrobenzofuran analogs of type 48 can be prepared from a known compound, methyl 5-nitro-2,3-dihydro-2-benzofurancarboxylate 41 (Cham. Pharm. Bull. 1989, 37, 2361–2368). The nitro group of structure 41 can be converted to the Cbz-protected aniline 42 by using the method described above for the indoline analogs. Reduction of the ester to the alcohol also as described above provides 43. This material can be protected as an appropriate ether derivative 44, or deoxygenated to the methyl intermediate 45 or oxidized to the aldehyde 46 via a Swern oxidation. Olefination of the aldehyde provides intermediates of type 47 which can be reduced via catalytic hydrogenation later in the synthesis. The remaining steps which lead 44, 45, 47 to the desired oxazolidinone analogs of type 48 are similar to these described in Charts I–IV.

Tetrahydroquinolines

Chart VI illustrates the synthesis of requisite 6-amino-2-alkyl-ttetrahydroquinolines analogs 58. Structure 51 can be prepared through the reduction of a known compound, methyl 6-nitro-2-quinolinecarboxylate 49, to the corresponding alcohol 50 followed by the protection of the alcohol group with an appropriate protecting group such as a silyl ether. The alcohol can also be converted to the aldehyde 52 via Swern oxidation. Olefination of the aldehyde provides alkenes of type 53. Structure 53 can be reduced to the aminoquinolines 54 with stannous chloride. Hydrogenation of materials 54 in the presence of platinum oxide provides the requisite 6-amino-2-alkyl-tetrahydroquinolines 55 as racemic mixtures. In the case of the 2-methyl derivative, the synthesis may be shortened by starting with commercially available 6-nitro-2-methylquinoline 56. The remaining steps that lead structure 57 to the final oxazolidinone analogs 58 are similar to the methods described in Chart I–V.

Benzoxazines and Benzothiazines

Chart VII depicts the preparation of the 7-amino-3-alkyl-3,4-dihydro-2H-1,4-benzoxazines and 7-amino-3-methyl-3,4-dihydro-2H-1,4-benzothiazins. Starting from structure 59, 7-amino-3-methyl-3,4-dihydro-2H-1,4-benzothiazins, 2,5-dinotrophenol, the formation of the triflate 60 followed by displacement with methylthiolate provides 61. Reduction of the nitro groups with Raney nickel or stannous chloride affords the bisaniline 62 (Y=S), which can be converted to the bis-phthalimid 63 (Y=S) with $BBr_3$ in a suitable solvent such as in $CH_2Cl_2$. Removal of the methyl group according to the procedure of Young et al (Tetrahedron Lett. 1984, 25, 1753–1756) affords the thiophenol 64 (Y=S). Alternatively, treatment of 2,5-diaminoanisole 62 (X=O) with excess phthalic anhydride affords the bis-phthalimide 63 (Y=O). Structure 63 then can be converted to the phenol 64 (Y=O) with $BBr_3$ in a suitable solvent such as $CH_2Cl_2$.

O— or S-alkylation of the phenol derivatives 64 with an appropriate α-chloroketone (R=alkyl) or methyl chloropyruvate (R=$CO_2$Me) in the presence of potassium iodide and a suitable base, such as potassium carbonate provides intermediates of type 65. Bis-deprotection of the amino groups with hydrazine is accompanied by cyclization to the imines 66 (R=alkyl, $CO_2CH_3$). Reduction of the imines with sodium borohydride or sodium cyanoborohydride will afford the desired 7-amino-3-substituted-3,4-dihydro-2H-1,4-benzoxazines 67 (Y=O) and 7-amino-3-substituted-3,4-dihydro-2H-1,4-benzothiazins 67 (Y=S) as racemic mixtures 67 (R=alkyl or $CO_2$Me). These compounds can be bis-protected with Cbz-chloride to give intermediates 68. The ester side chain can be manipulated as described above to allow the preparation of other variously substituted analogs. The remaining steps that lead structure 68 to the final oxazolidinone analogs 69 are similar to the methods described in Chart I–V.

Another method for the preparation of benzothiophenes is illustrated in Chart XI. Chart XI shows the synthesis of 2-substituted-2,3-dihydro-1-benzothiophene analogs. Beginning with commercially available 2-chloro-5-nitrobenzaldehyde 104 condensation with methyl thioglycolate and subsequent decarboxylation gives 105 (J. Amer. Chem. Soc. 1948, 70, 1955–1958). Oxidation to the sulfone 106, followed by hydrogenation and protection of the resulting amine with the 2,5-dimethylpyrrole group (Synthesis, 1998, 1599–1603) gives 107. Regioselective metalation with n-butyllithium or lithium bis(trimethylsilyl)amide and alkylation with an appropriate electrophile gives 108. Reduction of the sulfone with lithium aluminum hydride followed by removal of the protecting group and Cbz-protection gives 110. The sulfone in 108 can be maintained in the protecting group manipulation to give the intermediate 113. The remaining steps which lead 110 and 113 to the desired oxazolidinone analogs of type 111, 112, and 114 are similar to those described in Charts I–IV.

Tetrahydroquinoxalines

Chart VIII illustrates the preparation of the 2-alkyl-1,2,3,4-tetrahydro-6-quinoxalinylamine analogs. Condensation of the commercially available 1-chloro-2,4-dinitrobenzene 75 with an appropriately protected amino alcohol derivative 72 provides intermediates of structure 76. The aniline nitrogen of intermediates 76 can be protected with the Boc-group to give 77. Removal of the O-protecting group followed by mesylation provides 78. Treatment of mesylates with hydrogen in the presence of an appropriate catalyst at high dilution results in simultaneous reduction of the nitro-groups and ring closure to yield the desired 2-alkyl-1,2,3,4tetrahydro-6-quinoxalinylamines 79. The remaining steps that lead structure 79 to the final oxazolidinone analogs 82 are similar to the methods described in Chart I–V.

2,3-dihydro-1,4-benzoxathines

Chart IX illustrates the preparation of 3-substituted-2,3-dihydro-1,4-benzoxathiine analogs from a known know compound 83, 2-(benzyloxy)-4-nitrobenzenethiol (J. Am. Chem. Soc. 1950, 72, 3420). Simultaneous reduction of the nitro group and removal of the benzyl moiety via catalytic hydrogenation in the presence of an appropriate catalyst and treatment with benzylchloroformate provides the protected aniline 84. The treatment of this material with ethyl α-bromoacrylate 85 according to the method described in Martin et.al. (J. Org. Chem. 1974, 39, 1811–1814) provides the 1,4-benzoxathian intermediate 86. The ester can be reduced to the alcohol 87, then converted to the olefins 89 or protected as an ether 90, or deoxygenated to give 91. The remaining steps that lead structure 89, 90 and 91 to the final oxazolidinone analogs 92 are similar to the methods described in Chart I–V.

If desirable, the sulfur atom can be oxidized to the sulfoxide or sulfone at various stages in the synthesis by well-known methods.

3,4-dihydro-2H-1,4-benzothiazines

Chart X depicts the synthesis of 2-substituted-3,4-dihydro-2H-1,4-benzothiazine analogs. The treatment of a commercially available compound 93 with methanethiol provides compound 94. Demethylation of the sulfur according to the method of Young (Tetrahedron Lett. 1984, 25, 1753–1756) followed by reduction of the nitro groups with stannous chloride in refluxing ethanol provides the diaminothiophenol 95. The treatment of 95 with ethyl α-bromoacrylate 85 according to the method of described in Martin et.al. (J. Org. Chem. 1974, 39, 1811–1814) provides 1,4-benzothiazine intermediate 96. Biz-protection with 2 equivalents of benzyl chloroformate provides compound 97. The ester 97 can be converted to the desired analogs 103 via methods already described above.

These compounds are useful for the treatment of microbial infections, including ophthalmologic infections, in humans and other warm blooded animals, under both parental and oral administration.

The pharmaceutical compositions of this invention may be prepared by combining the compounds of Formula I of this invention with a solid or liquid pharmaceutically acceptable carrier and, optionally, with pharmaceutically acceptable adjuvants and excipient employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compounds of formula I according to this invention.

The quantity of active component, that is the compound of formula I according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds according to formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of formula I according to this invention are advantageously administered orally in solid and liquid dosage forms.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA. The activity of compounds of this invention against *Staphylococcus aureus, Staphylococcus epidermidis, Streptococcus pneumoniae, Enterococcus faecalis, Moraxella catarrhalis* and *H. influenzae* is shown in Table 1.

TABLE 1

Antibacterial Activity of Oxazolidinones, Minimum Inhibitory Concentration (μg/mL)

| EXAMPLE # | S.A.[1] | M.CAT.[2] |
|---|---|---|
| 3 | 4 | 4 |
| 4 | 1 | 4 |
| 5 | 2 | 4 |
| 6 | <0.5 | 1 |
| 7 | 4 | 8 |
| 8 | 8 | 16 |
| 9 | 2 | 8 |
| 10 | 4 | 8 |
| 11 | 1 | 4 |
| 12 | <0.5 | 1 |
| 14 | 2 | 4 |
| 15 | <0.5 | 1 |
| 17 | 4 | 8 |
| 18 | <0.5 | 2 |
| 19 | 4 | 16 |
| 20 | 4 | 16 |
| 21 | 2 | 4 |
| linezolid | 4 | 8 |
| eperezolid | 4 | 8 |
| vancomycin | 1 | >32 |

No. 1 is Methicillin-susceptible *S. aureus* UC® 9213. No. 2 is *Moraxella catarrhalis* UC® 30610. Minimum inhibitory concentration: lowest concentration of drug (μg/mL) that inhibits visible growth of the organism.

EXAMPLE 1

N-({(5S)-3-[1-(2-Fluoroethyl)-2-methyl-2,3-dihydro-1H-indol-5-yl]-2-oxo-1,3-oxazolidin-5-yl}methyl)acetamide

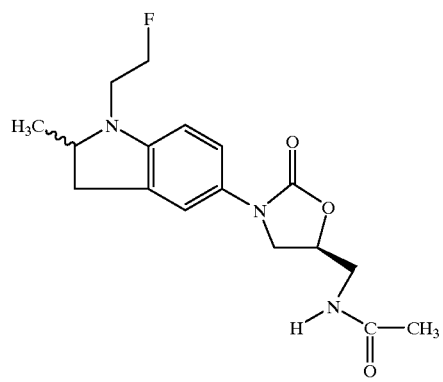

Step 1 Preparation of 2-methyl-5-nitro-1H-indole

2-Methylindole (8.4 g, 64 mmol) in con. $H_2SO_4$ (50 mL) is cooled to −5° C. A solution of $NaNO_3$ (5.4 g, 63.5 mmol) in $H_2SO_4$ (80 mL) is added dropwise. After addition, the mixture is poured over ice (800 g). The resulting dark brow solid is collected and washed with cold water and dried. This solid is heated in $CH_2Cl_2$ (220 mL) and the liquid is decanted from the remaining solid. The solvent is removed in vacuo and the residue is purified on silica gel with 15% EtAOc/hexane to give 2.5 g (22%) of the title compound. MS (EI) m/z 176 ($M^+$), Anal. Calcd for $C_9H_8N_2O_2$: C, 61.36; H, 4.58; N, 15.90. Found: C, 61.08; H, 4.64; N, 15.80.

Step 2 Preparation of 2-methyl-5-nitroindoline

The previous indole (4.43 g, 25.2 mmol) in AcOH (250 mL) is treated with $NaBH_3CN$ (75.5 mmol) in portions. After addition is complete the reaction is stirred at room temperature for 30 minutes. The reaction is diluted with water (2000 mL) and the pH is adjusted to 7 with 50% NaOH. The mixture is extracted with EtOAc and theorganic extracts are washed with saturated $NaHCO_3$, brine and dried ($Na_2SO_4$). The solvent is removed and the residue is purified on silica gel with 0–20% EtOAc/hexane gradient to give 2.62 g. the title compound.

Step 3 Preparation of benzyl 5-{[(benzyloxy)carbonyl]amino}-2-methyl-1-indolinecarboxylate The nitroindoline (2.62 g, 14.7 mmol) and 10% Pd/C (300 mg) are placed in MeOH (100 mL) under an atmosphere of hydrogen. The mixture is stirred vigorously for 5 hours. The reaction is filtered and the solvent removed in vacuo. The residue is dissolved in 3:1 acetone/water (150 mL) and $NaHCO_3$ (4.9 g, 58.9 mmol) is added followed by benzylchloroformate (4.4 mL, 31 mmol). The reaction is stirred 20 minutes, diluted with water (100 mL) and extracted with EtOAc. The organic extracts are washed with water, brine and dried ($Na_2SO_4$). The solvent is removed to give a syrup that is purified on silica gel with 0–15% EtOAc/hexane gradient to give 3.53 g (58%) of the title compound as an off white solid. Mp 107–111° C.

Step 4 Preparation of benzyl 5-[(5R)-5-(hydroxymethyl)-2-oxo-1,3-oxazolidin-3-yl]-2-methyl-1-indolinecarboxylate The previous compound (417 mg, 1 mmol) is dissolved in dry THF, cooled to −78° C. and treated with n-BuLi (1.6 M in hexane, 0.63 mL, 1.02 mmol). After 15 minutes R-(−)-glycidyl butyrate (0.14 mL, 1.01 mmol) and is added and the reaction is allowed to warm to room temperature overnight. The mixture is partitioned between $CH_2Cl_2$ and water. The organis layer is washed with brine and dried ($Na_2SO_4$). Removal of solvent gave a residue which is purified on silica gel with a 0–3% MeOH/$CH_2Cl_2$ gradient to give 0.26 g (68%) the title compound as solid: mp 129–132° C. HRMS (EI) calcd for $C_{21}H_{22}N_2O_5$ 382.1529, found 382.1518. $[\alpha]^{25}{}_D$=−33° (c 0.95, DMSO). Anal. Calcd for $C_{21}H_{22}N_2O_5$: C, 65.96; H, 5.80; N, 7.32. Found: C, 65.80; H, 5.69; N, 7.31.

Step 5 Preparation of benzyl 5-{(5S)-5-[(acetylamino)methyl]-2-oxo-1,3-oxazolidin-3-yl}-2-methyl-1-indolinecarboxylate The previous compound (2.46 g, 6.43 mmol) is dissolved in $CH_2Cl_2$ and cooled to 0° C. Triethylamine (0.98 mL, 7.08 mmol) and Nosyl-Cl (1.5 g, 6.75 mmol) are added. The reaction is stirred at room temperature for 20 minutes and washed with saturated $NaHCO_3$, brine and dried ($Na_2SO_4$). Removal of solvent gave an amber syrup that is combined with 1:1:1 MeCN/i-PrOH/30% $NH_4OH$ (150 mL). This solution is placed under a dry-ice condenser and heated to 60° C. for 6 hours. The solvent is removed in vacuo and the residue is dissolved in $CH_2Cl_2$ (50 mL) and treated with pyridine (1.0 mL, 12.9 mmol) and acetic anhydride (9.65 mL). After 20 minutes the reaction is washed with water, brine and dried ($Na_2SO_4$). Removal of solvent gave a residue that is purified on silica gel with 1–3% MeOH/$CH_2Cl_2$ gradient to give 1.8 g (66%) the title compound as a white solid: mp 170–175° C.; HRMS (EI) calcd for $C_{23}H_{25}N_3O_5$ 423.1794, found 423.1801. $[\alpha]^{25}{}_D$=−14° (c 1.02, DMSO). Anal. Calcd for $C_{23}H_{25}N_3O_5$: C, 65.24; H, 5.95; N, 9.92. Found: C, 64.92; H, 6.13; N, 9.84.

Step 6 N-{[(5S)-3-(2-methyl-2,3-dihydro-1H-indol-5-yl)-2-oxo-1,3-oxazolidin-5-yl]methyl}acetamide The previous compound (1.47 g, 3.5 mmol) is dissolved in 1:1 MeOH/$CH_2Cl_2$ (75 mL) and 10% Pd/C (100 mg) is added. The mixture is stirred vigorously under an atmosphere of hydrogen for three hours. The reaction is filtered and the solvent is removed in vacuo to give 0.98 g (98%) of product as a pink solid.

Step 7 N-({(5S)-3-[1-(2-fluoroethyl)-2-methyl-2,3-dihydro-1H-indol-5-yl]-2-oxo-1,3-oxazolidin-5-yl}methyl)acetamide The previous compound (0.48 g, 1.7 mmol) is placed in MeCN (10 mL) and water (1 mL). 1-Bromo-2-fluoroethane (0.16 mL, 2.16 mmol) and $K_2CO_3$ (0.4 g, 2.5 mmol) are added and the reaction is heated to reflux for 5 hours. Four more equivalents of 1-bromo-2-fluoroethane and $K_2CO_3$ are added and the reaction is refluxed an additional 2 days. The solvent is removed in vacuo and the crude material is purified on silica gel with 0.8–1.5% MeOH/$CH_2Cl_2$ gradient to give 522 mg (94%) the title compound as solid: mp 127–130° C.; HRMS (FAB) calcd for $C_{17}H_{22}FN_3O_3+H_1$ 336.1723, found 336.1721. Anal. Calcd for $C_{17}H_{22}FN_3O_3$: C, 60.88; H, 6.61; N, 12.53.Found: C, 60.58; H, 6.62; N, 12.31.

EXAMPLE 2

N-{[(5S)-3-(1-Glycoloyl-2-methyl-2,3-dihydro-1H-indol-5-yl)-2-oxo-1,3-oxazolidin-5-yl]methyl}acetamide

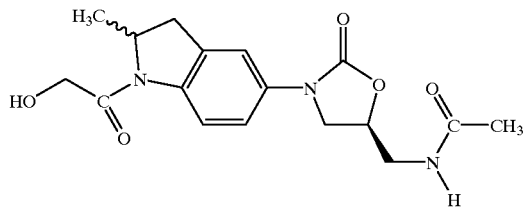

The deprotected material N-{[(5S)-3-(2-methyl-2,3-dihydro-1H-indol-5-yl)-2-oxo-1,3-oxazolidin-5-yl]methyl}acetamide (0.48 g, 1.66 mmol) (EXAMPLE 1, Step 6) and triethylamine (0.35 mL, 2.5 mmol) are dissolved in $CH_2Cl_2$ (10 mL). Acetoxyacetylchloride (0.233 mL, 2.16 mmol) is added along with additional $CH_2Cl_2$ (25 mL). After 20 minutes the mixture is diluted with $CH_2Cl_2$ (200 mL) and washed with water, brine and dried ($Na_2SO_4$). Removal of solvent gave a residue that is dissolved in MeOH (20 mL) and $CH_2Cl_2$ (80 mL). Potassium carbonate (200 mg) is added and the reaction is stirred for 20 minutes and evaporated to dryness. The residue is purified on silica gel with 2%

MeOH/CH$_2$Cl$_2$ to give 0.5 g (86%) of an off white solid: mp 130–133° C.; HRMS (FAB) calcd for C$_{17}$H$_{21}$N$_3$O$_5$+H$_1$ 348.1559, found 348.1569.Anal. Calcd for C$_{17}$H$_{21}$N$_3$O$_5$: C, 58.78; H, 6.09; N, 12.10.Found: C, 58.60; H, 6.27; N, 11.53.

EXAMPLE 3

N-({(5S)-3-[(2R)-1-Glycoloyl-2-methyl-2,3-dihydro-1H-indol-5-yl]-2-oxo-1,3-oxazolidin-5-yl}methyl)acetamide

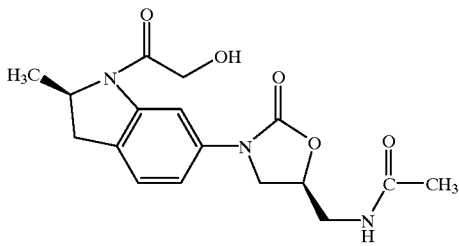

The product of EXAMMPLE 2 (0.4 g) is resolved by chiral chromatography using a chiralcel OJ column with 0.5 mL/min EtOH to give the title compound (145 mg) as a glassy solid. mp 162–167° C.; [α]$^{25}_D$=−78° (c 0.94, DMSO).

Also, N-({(5S)-3-[(2S)-1-glycoloyl-2-methyl-2,3-dihydro-1H-indol-5-yl]-2-oxo-1,3-oxazolidin-5-yl}methyl)acetamide is isolated from the separation (95 mg). mp 91–100° C.; [α]$^{25}_D$=34° (c 0.96, DMSO).

EXAMPLE 4

N-({(5S)-3-[(2R)-1-Formyl-2-methyl-2,3-dihydro-1H-indol-5-yl]-2-oxo-1,3-oxazolidin-5-yl}methyl)acetamide

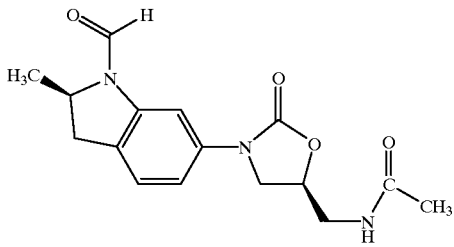

Step 1 Preparation of benzyl (2R)-5-[(5R)-5-(hydroxmethyl)-2-oxo-1,3-oxazolidin-3-yl]-2-methyl-2,3-dihydro-1H-indole-1-carboxylate The product of EXAMPLE 1, Step 4 (7.4 g) is resolved by chiral chromatography using a chiralcel OJ column with 0.5 mL/min EtOH to give 2.06 g as benzyl (2R)-5-[(5S)-5-(hydroxymethyl)-2-oxo-1,3-oxazolidin-3-yl]-2-methyl-2,3-dihydro-1H-indole-1-carboxylate the early eluting diastereomer; mp 144–145° C.; [α]$^{25}_D$=4° (c 0.96, DMSO). Also 2.05 g of the other diastereomer benzyl (2R)-5-[(5R)-5-(hydroxymethyl)-2-oxo-1,3-oxazolidin-3-yl]-2-methyl-2,3-dihydro-1H-indole-1-carboxylate (the title compound) is obtained. The title compound is then crystallized from 1:1 CHCl$_3$/Et$_2$O to give crystals suitable for X-ray analysis. The crystal structure is solved and the absolute stereochemistry showed it is the title compound. Mp 162–164° C.; [α]$^{25}_D$=−72° (c 0.96, DMSO).

Step 2 Preparation of benzyl (2R)-6-{(5S)-5-[(acetylamino)methyl]-2-oxo-1,3-oxazolidin-3-yl}-2-methyl-2,3-dihydro-1H-indole-1-carboxylate Following the procedure described in EXAMPLE 1, Step 5, using the above compound as the starting material, the title compound is obtained as a ywllow solid. mp 201–203° C.; [α]$^{25}_D$=−50° (c 0.92, DMSO).Anal. Calcd for C23H25N3O5: C, 65.24; H, 5.95; N, 9.92 Found: C, 65.36; H, 5.99; N, 9.86.

Step 3 Preparation of N-({(5S)-3-[(2R)-1-formyl-2-methyl-2,3-dihydro-1H-indol-5-yl]-2-oxo-1,3-oxazolidin-5-yl}methyl)acetamide The above product (200 mg, 0.47 mmol) and 10% Pd/C are placed in 20% CH2Cl2/MeOH (20 mL) under an atmosphere of hydrogen. The reaction is stirred vigorously for 2 hours and filtered. The solvent is evaporated and the residue is dissolved in CH$_2$Cl$_2$ (20 mL) and treated with Hunig's base (0.098 mL, 0.57 mmol), formic acid (0.018 mL, 0.47 mmol), and diethylcyanophosphonate (0.086 mL, 0.57 mmol), are added. The mixture is stirred at room temperature for 16 hours and the solution is washed with water, brine and dried (Na2SO4). The solvent is evaporated and the residue is purified on silica gel with 1–3% MeOH/CH2Cl2 gradient to give 0.14 g of the title compound as a pinke solid: mp 158–159° C.; HRMS (EI) calcd for C16H19N3O4 318.14545, found 318.1441.

[α]$^{25}$D=−58° (c 0.88, DMSO). Anal. Calcd for C16H19N3O4: C, 60.56; H, 6.03; N, 13.24. Found: C, 59.201; H, 6.18; N, 12.83.

EXAMPLE 5

N-({(5S)-3-[(2R)-1-Formyl-2-methyl-2,3-dihydro-1H-indol-5-yl]-2-oxo-1,3-oxazolidin-5-yl}methyl)propanamide

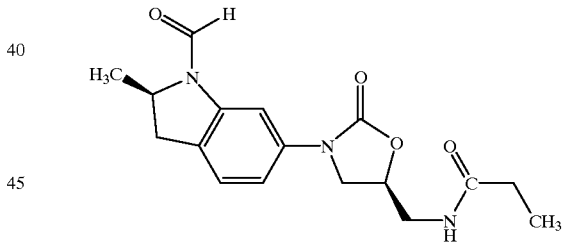

Step 1 Preparation of benzyl (2R)-2-methyl-5-{(5S)-2-oxo-5-[(propionylamino)methyl]-1,3-oxazolidin-3-yl}-2,3-dihydro-1H-indole-1-carboxylate Using the product of Example 4, Step 1 as the starting material and following the procedure described in EXAMPLE 1, Step 5, except propionylchloride is used in place of acetic anhydride, the title compound is obtained as solid; mp 181–183° C.; [α]$^{25}$D=−50°. (c 0.87, DMSO).Anal. Calcd for C24H27N3O5: C, 65.89; H, 6.22; N, 9.60.Found: C, 65.89; H, 6.26; N, 9.38.

Step 2 N-({(5S)-3-[(2R)-1-formyl-2-methyl-2,3-dihydro-1H-indol-5-yl]-2-oxo-1,3-oxazolidin-5-yl}methyl)propanamide Following the procedure described in EXAMPLE 4, Step 3, but using the above product as starting material (200 mg, 0.46 mmol), the title compound is obtained (134 mg) as a pink solid: mp 118–119° C.; HRMS (EI) calcd for C17H21N3O4 331.1532, found 332.1610 [α]$^{25}$D=–52° (c 0.64, DMSO).Anal. Calcd for C17H21N3O4: C, 61.62; H, 6.39; N, 12.68. Found: C, 60.68; H, 6.48; N, 12.36.

EXAMPLE 6

N-({(5S)-3-[(2R)-1-Formyl-2-methyl-2,3-dihydro-1H-indol-5-yl]-2-oxo-1,3-oxazolidin-5-yl}methyl)ethanethioamide

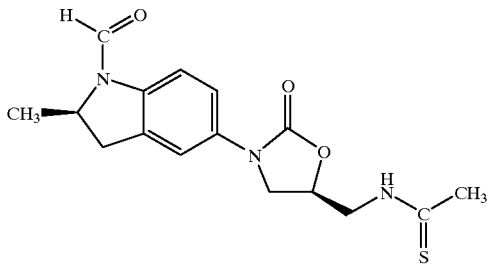

Step 1 Preparation of (2R)-2-methyl-5-nitro-2,3-dihydro-1H-indole (2R)-2-methyl-5-nitro-2,3-dihydro-1H-indole is prepared above by separating the corresponding 2-methyl-5-nitro-2,3-dihydro-1H-indole via chiral chromatography to give the pure enantiomers. 2R enantiomer data: mp 63–64° C.; [α]$^{25}$D=167° (c 0.98, chloroform). Anal. Calcd for C9H10N2O2: C, 60.66; H, 5.66; N, 15.72.Found: C, 60.50; H, 5.70; N, 15.48.

2S enantiomer is also obtained: mp 63–64° C.; [α]$^{25}_D$-162° (c 0.97, chloroform); Anal. Calcd for C9H10N2O2: C, 60.66; H, 5.66; N, 15.72.Found: C, 60.38; H, 5.76; N, 15.35.

Step 2 benzyl (2R)-5-{[(benzyloxy)carbonyl]amino}-2-methyl-2,3-dihydro-1H-indole-1-carboxylate The 2R-indoline from the above resolution (7.5 g, 42.1 mmol) and 10% Pd/C (0.7 g) in MeOH (100 mL) is hydrogenated on a Parr shaker at 30 psi. The mixture is filtered and solvent is evaporated. The residue is taken up in dry THF and solid NaHCO3 (7.3 g, 85 mmol) is added followed by benzyl chloroformate (12.6 mL, 88 mmol). The mixture is stirred overnight at room temperature and partitioned between water and EtOAc. The organic layer is washed with brine and dried (Na2SO4). Removal of solvent gave the title compound which is then crystallized from EtOAc, 13.6 g (78%); [α]$^{25}_D$-30° (c 0.93, chloroform).

Anal. Calcd for C25H24N2O4: C, 72.10; H, 5.81; N, 6.73.Found: C, 72.09; H, 5.85; N, 6.68.

Step 3 benzyl (2R)-5-[(5R)-5-(hydroxymethyl)-2-oxo-1,3-oxazolidin-3-yl]-2-methyl-2,3-dihydro-1H-indole-1-carboxylate Following the procedure described in EXAMPLE 1, Step 4, but using the above product as the starting material (10 g, 24 mmol) with butyllithium (1.6 M, 15.2 mL, 24.3 mmol), and R-(–)-glycidyl butyrate (3.44 mL, 24.3 mmol), the title compound is obtained as a white solid (8.05 g).

Step 4 benzyl (2R)-2-methyl-5-((5R)-5-{[(methylsulfonyl)oxy]methyl}-2-oxo-1,3-oxazolidin-3-yl)-2,3-dihydro-1H-indole-1-carboxylate The above product (8.05 g, 21.07 mmol) is dissolved in CH2Cl2 and cooled to 0° C. This solution is treated with triethylamine (1.1 equiv.) and methanesulfonyl chloride (1.1 equiv.) and allowed to warm to room temperature. The reaction is washed with 2 N HCl, saturated NaHCO3, brine and dried (Na2SO4). Removal of solvent invacuo gave the title compound which is then purified on silica gel with 5% MeCN/CH2Cl2 as a white solid (9.6 g 99%). Mp 72–73° C.; [α]$^{25}_D$=–74° (c 0.97, DMSO).Anal. Calcd for C22H24N2O7S: C, 57.38; H, 5.25; N, 6.08; S, 6.96.Found: C, 57.22; H, 5.26; N, 6.00.

Step 5 benzyl (2R)-5-[(5R)-5-(azidomethyl)-2-oxo-1,3-oxazolidin-3-yl]-2-methyl-2,3-dihydro-1H-indole-1-carboxylate The above product (9.5 g, 20.65 mmol) and NaN3 (5.37 g, 82.6 mmol) are placed in dry DMF (100 mL) and heated at 65° C. overnight. The reaction is cooled and diluted with EtOAc (500 mL) and washed with water (3×100 mL), brine and dried (Na2SO4). Removal of solvent gave the title compound as a white solid 7.11 g (85%); mp 192–193° C.; Anal. Calcd for C21H21N5O4: C, 61.91; H, 5.20; N, 17.19. Found: C, 61.78; H, 5.19; N, 17.05.

Step 6 benzyl (2R)-5-[(5S)-5-(aminomethyl)-2-oxo-1,3-oxazolidin-3-yl]-2-methyl-2,3-dihydro-1H-indole-1-carboxylate The above product (6.9 g, 16.9 mmol) is dissolved in dry THF (75 mL). A solution of triphenylphosphine (5.3 g, 20 mmol) in THF (20 mL) is added dropwise. The reaction is stirred at room temperature for 4 hours. Water (25 mL) is added and the mixture is heated to 65° C. overnight. The reaction is concentrated in vacuo, diluted with CH2Cl2 and washed with saturated NaHCO3, brine and dried (Na2SO4). Removal of solvent gave the title compound which is then purified on silica gel with a 0–10% MeOH/CH2Cl2 gradient. Product is isolated as a white solid: mp 120–122° C.; Anal. Calcd for C21H23N3O4: C, 66.13; H, 6.08; N, 11.02. Found: C, 65.85; H, 6.18; N, 10.86.

Step 7 benzyl (2R)-5-{(5S)-5-[(acetylamino)methyl]-2-oxo-1,3-oxazolidin-3-yl}-2-methyl-2,3-dihydro-1H-indole-1-carboxylate The above product (5.3 g, 13.9 mmol) is dissolved in CH2Cl2 and pyridine (1.21 mL, 15 mmol) is added followed by acetic anhydride (1.42 mL, 15 mmol). After 1 hour the reaction is diluted with CH2Cl2, washed with 1 N HCl, saturated NaHCO3, brine and dried (Na2SO4). Removal of solvent gave the title compound as a white solid.

Step 8 N-({(5S)-3-[(2R)-2-methyl-2,3-dihydro-1H-indol-5-yl]-2-oxo-1,3-oxazolidin-5-yl}methyl)ethanethioamide hydrobromide The acetamide from the previous reaction (0.21 g, 0.5 mmol) and Lawesson's reagent (0.1 g, 0.25 mmol) are refluxed in toluene. The solvent is removed in vacuo and the residue is chromatographed on silica gel with 0–5% MeOH/CH2Cl2 gradient. The thioamide is isolated as a white foam 0.21 g. The thioamide thus prepared (0.54 g, mmol) is placed in 30% HBr/HOAc (20 mL) at room temperature for 30 minutes. The reaction is diluted with Et2O and the precipitated title compound is isolated via filtration. The product is dissolved in MeOH/CH2Cl2 and evaporated to dryness in vacuo (3×). The residue is dried in hi-vac.

Step 9 N-({(5S)-3-[(2R)-1-formyl-2-methyl-2,3-dihydro-1H-indol-5-yl]-2-oxo-1,3-oxazolidin-5-yl}methyl)ethanethioamide The above HBr salt (1.2 mmol) is placed in CH2Cl2 and Hunig's base (1 ML) is added. The solvent is evaporated and the residue dissolved in CH₂Cl₂ and stripped of solvent (2x) and then dried in vacuo. In a separate flask 99% formic acid (0.45 mL) and acetic anhydride (1.03 mL) are heated at 70° C. for 2 hours cooled and diluted with THF (10 mL). The free base generated above is dissolved in THF and added to the mixed anhydride. The reaction is stirred at room temperature overnight, diluted with CH₂Cl₂, washed with water, brine and dried (Na₂SO₄). Removal of solvent gave a residue that is purified on silica gel with 0–3% MeOH/CH₂Cl₂ gradient. Product is isolated as a white foam: mp 95–96° C.; HRMS (FAB) calcd for C₁₆H₁₉N₃O₃S+H₁ 334.1225, found 334.1230.Anal. Calcd for C₁₆H₁₉N₃O₃S: C, 57.64; H, 5.74; N, 12.60; S, 9.62.Found: C, 51.93; H, 5.29; N, 10.81.

EXAMPLE 7

N-({(5S)-3-[(2R)-1-(2-Methoxyacetyl)-2-methyl-2,3-dihydro-1H-indol-5-yl]-2-oxo-1,3-oxazolidin-5-yl}methyl)acetamide

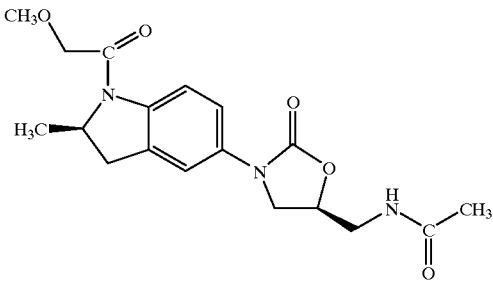

Step 1 Preparation of SN-({(5S)-3-[(2R)-2-methyl-2,3-dihydro-1H-indol-5-yl]-2-oxo-1,3-oxazolidin-5-yl}methyl)acetamide The product of EXAMPLE 6, Step 7 (5.0 g, 11.8 mmol) is hydrogenated in methanol on a Parr shaker at 20 psi using 10% Pd/C as catalyst. The reaction is filtered and the solvent removed in vacuo. The title compound is isolated as an amorphous solid 1.9 g (55%).

mp 56–57° C.

Step 2 Preparation of N-({(5S)-3-[(2R)-1-(2-methoxyacetyl)-2-methyl-2,3-dihydro-1H-indol-5-yl]-2-oxo-1,3-oxazolidin-5-yl}methyl)acetamide The above product (0.1 g, 0.35 mmol), EDC (70 mg, 0.36 mmol) and methoxyacetic acid (0.03 mL, 0.36 mmol) are stirred in THF for 5 hours. The reaction is diluted with CH₂Cl₂, washed with 2N HCl, saturated NaHCO₃, brine and dried (Na₂SO₄). Removal of solvent gave a residue that is purified on silica gel with 0–4% MeOH/CH₂Cl₂ gradient to give the title compound as a white solid: mp 174–175° C.; HRMS (FAB) calcd for C₁₈H₂₃N₃O₅+H₁ 362.1716, found 362.1725.Anal. Calcd for C₁₈H₂₃N₃O₅: C, 59.82; H, 6.41; N, 11.63.Found: C, 59.56; H, 6.40; N, 11.25.

EXAMPLE 8

2-((2R)-5-{(5S)-5-[(Acetylamino)methyl]-2-oxo-1,3-oxazolidin-3-yl}-2-methyl-2,3-dihydro-1H-indol-1-yl)-2-oxoethyl acetate

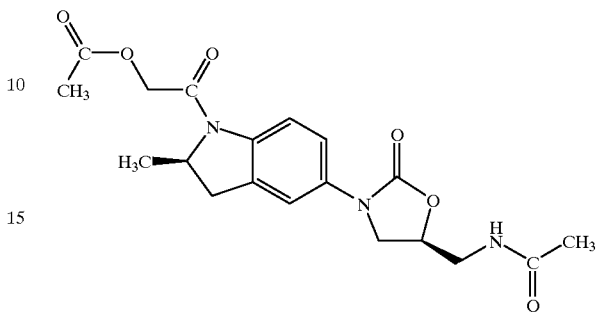

The product of EXAMPLE 7, Step 1 (0.1 g, 0.35 mmol) and NEt₃ (0.05 mL) are placed in dry THF and acetoxyacetyl chloride (0.04 mL, 0.36 mmol) is added. The reaction is stirred 1 hour, diluted with CH₂Cl₂ and washed with 2 N HCl, saturated NaHCO₃, brine and dried (Na₂SO₄). Removal of solvent provide the title compound which is then purified on silica gel with 0–4% MeOH/CH₂Cl₂ gradient to give product as a white solid: mp 186–187° C. HRMS (FAB) calcd for C₁₉H₂₃N₃O₆+H₁ 390.1665, found 390.1664.Anal. Calcd for C₁₉H₂₃N₃O₆: C, 58.60; H, 5.95; N, 10.79.Found: C, 58.01; H, 6.13; N, 10.60.

EXAMPLE 9

N-({(5S)-3-[(2R)-1-Acetyl-2-methyl-2,3-dihydro-1H-indol-5-yl]-2-oxo-1,3-oxazolidin-5-yl}methyl)acetamide

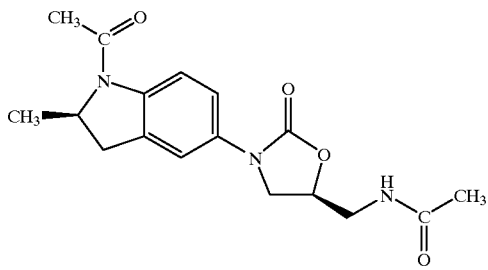

The product of EXAMPLE 7, Step 1 (0.5 g, 1.3 mmol) is dissolved in 30 mL of CH₂Cl₂ and cooled to 0° C. Triethylamine (0.3 g, 2.9 mmol) is added followed by acetyl chloride (0.12 mL, 1.6 mmol). This mixture is slowly warmed to room temperature. After one hour ~20 mg of additional acetyl chloride is added and the mixture is stirred at room temperature for an additional hour. The mixture is washed with water and dilute HCl. The organic phase is separated and washed with brine and dried over anhydrous Na₂SO₄. Filtration and removal of solvent gave 200 mg of an off-white solid (45%); mp 184–185° C.; HRMS (FAB) calcd for C₁₇H₂₁N₃O₄+H₁ 332.1610, found 332.1606. [α]$^{25}_D$ –71° (c 0.46, DMSO). Anal. Calcd for C₁₇H₂₁N₃O₄1/2H₂O: C, 59.99; H, 6.51; N, 12.35. Found; C, 60.30; H, 6.39; N, 12.11.

EXAMPLE 10

N-[((5S)-3-{(2R)-2-Methyl-1-[(methylamino)carbothioyl]-2,3-dihydro-1H-indol-5-yl}-2-oxo-1,3-oxazolidin-5-yl)methyl]acetamide

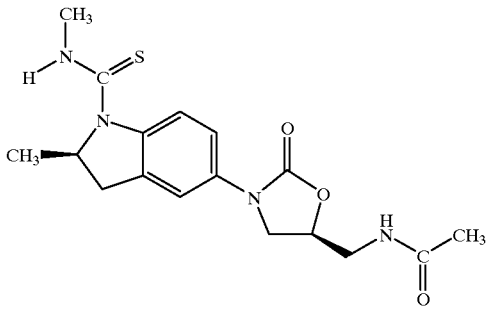

The product of EXAMPLE 7, Step 1 (0.5 g, 1.3 mmol) is dissolved in 30 mL of $CH_2Cl_2$ and cooled to 0° C. Triethylamine (0.3 g, 2.9 mmol) is added followed by methylthioisocyanate (0.12 g, 1.6 mmol). This mixture is slowly warmed to room temperature and stirred overnight. An additional ~30 mg of methylthioisocyanate is added and the mixture is stirred for 3 hours at room temperature. The mixture is washed with water and dilute HCl. The organic phase is separated and washed with brine and dried over anhydrous $Na_2SO_4$. Filtration and removal of solvent gave a yellow solid, which is chromatographed over silica gel with a $CH_2Cl_2$ to 4% $CH_3OH/CH_2Cl_2$ gradient. 410 mg of product is obtained as a white solid (84%); mp 109–111° C.; HRMS (FAB) calcd for $C_{17}H_{22}N_4O_3S+H1$ 363.1491, found 363.1495. $[\alpha]^{25}_D$ -118° (c 0.58, DMSO).

EXAMPLE 11

2-((2R)-5-{(5S)-5-[(Ethanethioylamino)methyl]-2-oxo-1,3-oxazolidin-3-yl}-2-methyl-2,3-dihydro-1H-indol-1-yl)-2-oxoethyl acetate

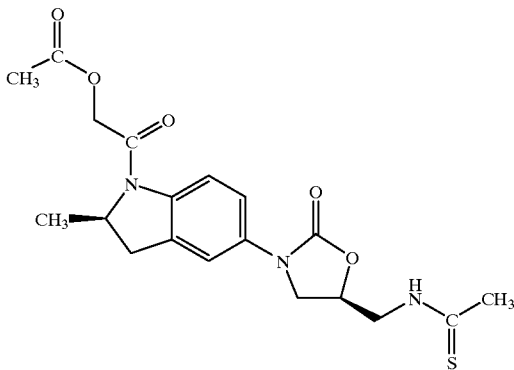

The product of EXAMPLE 7, Step 1 (0.3 g, 1.04 mmol) and Lawesson's reagent (0.42 g, 1.04 mmol) are refluxed in toluene for 4 hours. The solvent is removed and the residue is purified on silica gel with 0–4% $MeOH/CH_2Cl_2$ gradient to give the thioamide as a greenish foam 0.26 g. This thioamide (0.13 g, 0.43 mmol) and triethylamine (0.064 mL, 0.46 mmol) are placed in $CH_2Cl_2$ and acetoxyacetyl chloride (0.05 mL, 0.46 mmol) is added. The reaction is stirred at room temperature for 2 hour, diluted with $CH_2Cl_2$ and washed with saturated $NaHCO_3$ and dried ($Na_2SO_4$). Removal of solvent gave a residue that is purified on silica gel with 0–3% $MeOH/CH_2Cl_2$ gradient to give product as a white solid 70 mg (40% from thioamide). HRMS (FAB) calcd for $C_{19}H_{23}N_3O_5S+H_1$ 406.1436, found 406.1422. Anal. Calcd for $C_{19}H_{23}N_3O_5S$: C, 56.28; H, 5.72; N, 10.36; S, 7.91. Found: C, 54.41; H, 5.65; N, 8.90.

EXAMPLE 12

N-({(5S)-3-[(2R)-1-Glycoloyl-2-methyl-2,3-dihydro-1H-indol-5-yl]-2-oxo-1,3-oxazolidin-5-yl}methyl)ethanethioamide

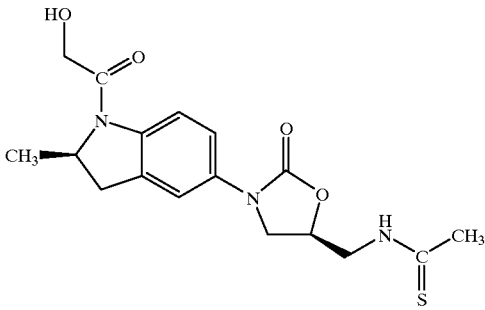

The product of EXAMPLE 11 (20 mg, 0.05 mmol) and $K_2CO_3$ (20 mg) are stirred in MeOH for 2 hours. The reaction is filtered and the solvent evaporated to give pure product as a white solid 18 mg (99%): mp 115–117° C.; HRMS (FAB) calcd for $C_{17}H_{21}N_3O_4S+H_1$ 364.1331, found 364.1317. Anal. Calcd for $C_{17}H_{21}N_3O_4S$: C, 56.18; H, 5.82; N, 11.56; S, 8.82. Found: C, 56.95; H, 6.58; N, 9.40.

EXAMPLE 13

N-{[(5S)-3-(1-Formyl-2-methyl-1,2,3,4-tetrahydro-6-quinolinyl)-2-oxo-1,3-oxazolidin-5-yl]methyl}acetamide

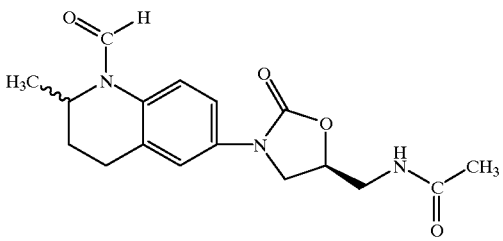

Step 1 Preparation of 2-methyl-6-quinolinamine

Tin(II) chloride dihydrate (60.4 g, 0.27 mol) and 2-methyl-6-nitroquinoline (8.4, 44.6 mmol) are stirred in ethanol and the mixture heated at reflux overnight. After cooling to room temperature, DI water (1.2 mL) is added and the solution made basic with sodium bicarbonate. The mixture is extracted with ethyl acetate (3×250 mL) and the combined organics dried ($Na_2SO_4$) and filtered. Solvent is evaporated to give a solid which is recrystallized from $CH_2Cl_2$ to give the title compound as crystals, 6.2 g (88%); mp187–189° C.; Anal. Calcd for $C_{10}H_{10\ N2}$: C, 75.92; H, 6.37; N, 17.71. Found: C, 75.88; H, 6.35; N, 17.60.

Step 2 Preparation of benzyl 6-{[(benzyloxy)carbonyl]amino}-2-methyl-3,4-dihydro-1(2H)-quinolinecarboxylate The above product (3.5 g, 22.1 mmol) and $PtO_2$ (0.2 g) in MeOH (40 mL) and con. $H_2SO_4$ (1.5 mL) is hydrogenated on a Parr shaker at 30 psi. The mixture is filtered and solvent is evaporated. The residue is taken up in Acetone (80 mL) and saturated aqueous NaHCO$_3$ (80 mL) and cooled to 0° C. Benzyl chloroformate (7.8 mL, 55 mmol) is added dropwise and the mixture allowed to warm to room temperature while stirring overnight. The mixture is partitioned between water and EtOAc. The organic layer is washed with water then brine and dried (Na$_2$SO$_4$). Solvent is evaporated and the residue chromatographed on silica gel using 25% EtOAc/Heptane eluant. The title compound is isolated as an off-white solid 9.4 g (98%); mp115–117° C.; Anal. Calcd for C$_{26}$H$_{26}$N$_2$O$_4$: C, 72.54; H, 6.09; N, 6.51.Found: C, 72.50; H, 6.05; N, 6.49.

Step 3 Preparation of benzyl 6-[(5R)-5-(hydroxymethyl)-2-oxo-1,3-oxazolidin-3-yl]-2-methyl-3,4-dihydro-1(2H)-quinolinecarboxylate Following the procedure described in EXAMPLE 1, Step 4, but using the above product as starting material, the title compound is. Purification by chromatography on silica gel using 1–2% MeOH/CH$_2$Cl$_2$ gradient gave product as an off-white foamy solid 5.0 g (59%); mp 99–102° C.; Anal. Calcd for C$_{22}$H$_{24}$N$_2$O$_5$: C, 66.65; H, 6.10; N, 7.07.Found: C, 66.60; H, 6.50; N, 6.92.

Step 4 Preparation of benzyl 6-{(5S)-5-[(acetylamino)methyl]-2-oxo-1,3-oxazolidin-3-yl}-2-methyl-3,4-dihydro-1(2H)-quinolinecarboxylate The above product (1.3 g, 3.3 mmol) is dissolved in CH$_2$Cl$_2$ (20 mL) and cooled to 0° C. Triethylamine (0.55 mL, 3.9 mmol) is added followed by 3-Nitrobenzenesulfonyl chloride (0.84 g, 3.8 mmol) and the mixture stirred 1.5 hours. The mixture is washed with H$_2$O then saturated NaHCO$_3$ and the organics dried (Na$_2$SO$_4$). The mixture is filtered and solvent evaporated. The residue is combined with CH$_3$CN (25 mL), IPA (25 mL), and 30%NH$_4$OH (25 mL). The solution is heated to 60° C. under a dry ice condenser for 7 hours. Solvent is evaporated and the residue dissolved in CH$_2$Cl$_2$ (25 mL). Pyridine (1.0 mL) and Acetic Anhydride (1.0 mL) is added and the mixture stirred 2 hours. The mixture is washed with H$_2$O then brine and dried (Na$_2$SO$_4$). The mixture is filtered, solvent evaporated and the residue chromatographed on silica gel using 0–4% MeOH/CH$_2$Cl$_2$ eluant. Product is isolated as a white foamy solid 1.1 g (76%); mp126–129° C.; HRMS (EI) calcd for C$_{24}$H$_{27}$N$_3$O$_5$ 437.1951, found 437.1961.

Step 5 Preparation of N-{[(5S)-3-(2-methyl-1,2,3,4-tetrahydro-6-quinolinyl)-2-oxo-1,3-oxazolidin-5-yl]methyl}acetamide The above product (1.0 g, 2.3 mmol) and 10% Pd/C(0.15 g) is dissolved in CH$_2$Cl$_2$ (25 mL) and MeOH (25 mL) and hydrogenated on a Parr shaker at 30 psi. The mixture is filtered and solvent evaporated to give the title compound as a solid, 67 g (97%); mp158–9° C.; HRMS (FAB) calcd for C$_{16}$H$_{21}$N$_3$O$_3$+H$_1$ 304.1661, found 304.1653.

Step 6 Preparation of N-{[(5S)-3-(1-formyl-2-methyl-1,2,3,4-tetrahydro-6-quinolinyl)-2-oxo-1,3-oxazolidin-5-yl]methyl}acetamide The above product (0.20 g, 0.66 mmol) and Formic Acid (0.06 ml,1.4 mmol) is stirred in CH$_2$Cl$_2$(20 mL). Diethyl cyanophosphonate (0.24 mL, 1.6 mmol) and Diisopropylethylamine (0.28 mL, 1.6 mmol) is added and the mixture stirred overnight. The mixture is washed (H$_2$O) dried (Na$_2$SO$_4$) filtered and solvent evaporated. The residue is chromatographed on silica gel using 1–4% MeOH/CH$_2$Cl$_2$ eluant. The title compound is isolated as a white solid 103 mg (47%); mp85–87° C.; HRMS (EI) calcd for C$_{17}$H$_{21}$N$_3$O$_4$ 331.1532, found 331.1544.

EXAMPLE 14

N-({(5S)-3-[(2R)-1-Formyl-2-methyl-1,2,3,4-tetrahydro-6-quinolinyl]-2-oxo-1,3-oxazolidin-5-yl}methyl)acetamide

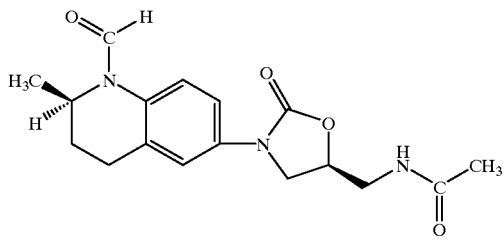

Step 1 Preparation of Benzyl (2R)-6-[(5R)-5-(hydroxymethyl)-2-oxo-1,3-oxazolidin-3-yl]-2-methyl-3,4-dihydro-1(2H)-quinolinecarboxylate The product of EXAMPLE 13, Step 3 is separated into its component diastereomers by preperative liquid chromatography using a 5×50 cm Chiralcell® OJ column at 35° C. eluting with EtOH (0.4 mL/min). The first eluting fraction is collected, solvent is removed by evaporation and the resulting solid recrystallized from MeOAc/Heptane. Absolute stereochemistry is determined by X-ray crystallography as the title compound. [α]$^{25}_D$–141°(DMSO); HRMS (FAB) calcd for C$_{22}$H$_{24}$N$_2$O$_5$+H$_1$ 397.1763, found 397.1754. The second eluting fraction is collected, solvent is removed by evaporation and the resulting solid recrystallized from MeOAc/Heptane. Absolute stereochemistry is determined by X-ray crystallography as Benzyl (2S)-6-[(5R)-5-(hydroxymethyl)-2-oxo-1,3-oxazolidin-3-yl]-2-methyl-3,4-dihydro-1(2H)-quinolinecarboxylate. [α]$^{25}_D$+81°(DMSO); HRMS (FAB) calcd for C$_{22}$H$_{24}$N$_2$O$_5$+H$_1$ 397.1763, found 397.1746.

Step 2 Preparation of Benzyl (2R)-6-{(5S)-5-[(acetylamino)methyl]-2-oxo-1,3-oxazolidin-3-yl}-2-methyl-3,4-dihydro-1(2H)-quinolinecarboxylate The above product, benzyl (2R)-6-[(5R)-5-(hydroxymethyl)-2-oxo-1,3-oxazolidin-3-yl]-2-methyl-3,4-dihydro-1(2H)-quinolinecarboxylate (3.1 g, 7.8 mmol) is used as starting material. Following the procedure described in EXAMPLE 13, Step 4 to give the title compound as an off-white solid (40%); mp 157–159° C.; HRMS (FAB) calcd for C$_{24}$H$_{27}$N$_3$O$_5$+H$_1$ 438.2029, found 438.2028.

Step 3 Preparation of N-({(5S)-3-[(2R)-1-formyl-2-methyl-1,2,3,4-tetrahydro-6-quinolinyl]-2-oxo-1,3-oxazolidin-5-yl}methyl)acetamide The above product (0.25 g, 0.57 mmol) and 10% Pd/C (0.03 g) is dissolved in CH$_2$Cl$_2$(20 mL) and MeOH (20 mL) and hydrogenated on a Parr shaker at 30 psi. The mixture is filtered and solvent evaporated to obtain intermediate amine which is reacted further as follows. Formic Acid (0.23 mL, 6.8 mmol) is added dropwise to Acetic Anhydride (0.51 mL, 5.0 mmol) and the mixture heated at 56° C. for 2 hours. After cooling to room temperature, dry THF (2 mL) is added followed by a solution of the above intermediate amine dissolved in THF (2 mL). The mixture is stirred overnight then solvent removed by evaporation. The residue is chromatographed on silica gel using 0–4% MeOH/CH$_2$Cl$_2$ eluant. Product is isolated as a white solid 150 mg (79%); mp 89–91° C., [α]$^{25}_D$ –106°(DMSO); HRMS (FAB) calcd for C$_{17}$H$_{21}$N$_3$O$_4$+H$_1$ 332.1610, found 332.1613.

EXAMPLE 15

N-({(5S)-3-[(2R)-1-Formyl-2-methyl-1,2,3,4-tetrahydro-6-quinolinyl]-2-oxo-1,3-oxazolidin-5-yl}methyl)ethanethioamide

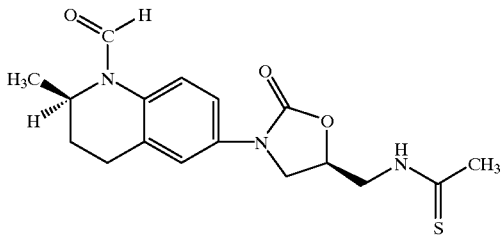

Step 1 Preparation of benzyl (2R)-6-{(5S)-5-[(ethanethioylamino)methyl]-2-oxo-1,3-oxazolidin-3-yl}-2-methyl-3,4-dihydro-1(2H)-quinolinecarboxylate The product of EXAMPLE 14, Step 2 (1.0 g, 2.3 mmol) and Lawesson's Reagent (0.50 g, 1.3 mmol) are stirred in Toluene (20 mL) at reflux for 2 hours. Solvent is removed by evaporation and the residue is chromatographed on silica gel using 0–4% MeOH/CH$_2$Cl$_2$ eluant. The title compound is isolated as a white solid 1.0 g (97%); HRMS (FAB) calcd for C$_{24}$H$_{27}$N$_3$O$_4$S+H$_1$ 454.1800, found 454.1813.

Step 2 Preparation of N-({(5S)-3-[(2R)-1-formyl-2-methyl-1,2,3,4-tetrahydro-6-quinolinyl]-2-oxo-1,3-oxazolidin-5-yl}methyl)ethanethioamide The above product (1.0 g, 2.2 mmol) is dissolved in Acetic Acid (10 mL). 30% HBr/Acetic Acid (20 mL) is added dropwise and the mixture stirred 1 hour. Et$_2$O (200 mL) is added to precipitate the intermediate amine as a salt. The Et$_2$O is decanted and Et$_2$O (200 mL) added again to wash. The Et$_2$O is decanted and H$_2$O (50 mL) added to dissolve the solid. The aqueous solution is made basic with saturated NaHCO$_3$. The product is extracted into CH$_2$Cl$_2$ (2×50 mL). The organics are dried (Na$_2$SO$_4$), filtered and solvent evaporated. The intermediate amine so obtained is reacted further as follows. Formic Acid (0.23 mL, 6.8 mmol) is added dropwise to Acetic Anhydride (0.51 mL, 5.0 mmol) and the mixture heated at 56° C. for 2 hours. After cooling to room temperature, dry THF (2 mL) is added followed by a solution of the above intermediate amine dissolved in THF (2 mL). The mixture is stirred overnight then solvent removed by evaporation. The residue is chromatographed on silica gel using 0–4% MeOH/CH$_2$Cl$_2$ eluant. The title compound is isolated as a white solid 150 mg (20%); mp 184–186° C.; [α]$^{25}_D$ –73°(DMSO); HRMS (FAB) calcd for C$_{17}$H$_{21}$N$_3$O$_3$S+H$_1$ 348.1382, found 348.1378.

EXAMPLE 16

N-{[(5S)-3-(4-Formyl-3-methyl-3,4-dihydro-2H-1,4-benzoxazin-7-yl)-2-oxo-1,3-oxazolidin-5-yl]methyl}acetamide

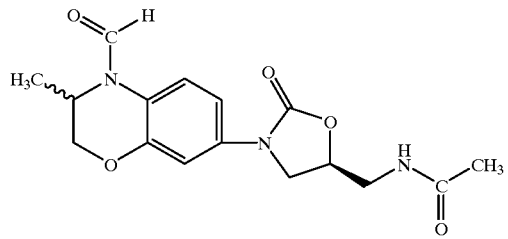

Step 1 Preparation of 2-[4-(1,3-dioxo-1,3-dihydro-2H-isoindol-2-yl)-2-methoxyphenyl]-1H-isoindole-1,3(2H)-dione 2,5-Diaminoanisole sulfate (40.7 g, 164 mmol) is converted to the free base by dissolving in H$_2$O (600 mL) and adding saturated NaOH until the solution reaches pH 11. The solution is extracted with Et$_2$O (3×300 mL), the combined extracts dried (Na$_2$SO$_4$), filtered and solvent removed to obtain free amine as a purple solid (6.5 g, 47 mmol). This material is dissolved in dry DMF (25 mL) with Phthalic Anhydride (17.2 g, 116 mmol) and the mixture stirred for 1 hour. Acetic Anhydride (20 mL) is added followed by Pyridine (10 mL) and the mixture heated at 90° C. for 4 hours. The solution is cooled to room temperature. The solid product is collected by filtration, washed (H$_2$O) and recrystallized from DMF as a pink solid 17.0 g (91% from free base); mp284–286° C. MS (EI) m/z (rel. intensity) 398 (M$^+$, 58), Anal. Calcd for C$_{23}$H$_{14}$N$_2$O$_5$: C, 69.34; H, 3.54; N, 7.03. Found: C, 69.40; H, 3.41; N, 7.05.

Step 2 Preparation of 2-[4-(1,3-dioxo-1,3-dihydro-2H-isoindol-2-yl)-3-hydroxyphenyl]-1H-isoindole-1,3(2H)-dione Boron Tribromide (19.9 mL, 211 mmol) is added dropwise at –78° C. to the above product (12.0 g, 30.1 mmol) in CH$_2$Cl$_2$ (300 mL) with overhead stirring. The thick mixture is allowed to reach room temperature and stirred overnight. The mixture is cautiously quenched with H$_2$O and filtered. The solid is washed (H$_2$O) and recrystallized from DMF and obtained as a pink solid 11.0 g (95%); mp>300° C. HRMS (EI) calcd for C$_{22}$H$_{12}$N$_2$O$_5$ 384.0746, found 384.0749.Anal. Calcd for C$_{22}$H$_{12}$N$_2$O$_5$: C, 68.75; H, 3.15; N, 7.29. Found: C, 66.53; H, 3.50; N, 7.15.

Step 3 Preparatio of 2-[4-(1,3-dioxo-1,3-dihydro-2H-isoindol-2-yl)-3-(2-oxopropoxy)phenyl]-1H-isoindole-1,3(2H)-dione The product of step 2 (1.0 g, 2.6 mmol), K$_2$CO$_3$ (0.8 g, 5.8 mmol) and KI (80 mg) are combined in Acetone (30 mL). Chloroacetone (0.43 mL, 5.4 mmol) is added and the mixture heated at reflux overnight. Solvent is evaporated and the solid taken up in hot MeOH and filtered. The solid is taken up in hot DMF, filtered and washed with MeOH, and obtained as a white solid (61%); mp.300° C. MS (EI) m/z (rel. intensity) 440 (M$^+$); Anal. Calcd for C$_{25}$H$_{16}$N$_2$O$_6$: C, 68.18; H, 3.66; N, 6.36. Found: C, 67.98; H, 3.62; N, 6.26.

Step 4 Preparation of Benzyl 7-{[(benzyloxy)carbonyl]amino}-3-methyl-2,3-dihydro-4H-1,4-benzoxazine-4-carboxylate 2-[4-(1,3-dioxo-1,3-dihydro-2H-isoindol-2-yl)-3-(2-oxopropoxy)phenyl]-1H-isoindole-1,3(2H)-dione (2.0 g, 4.5 mmol) is stirred as a suspension in dry THF. Hydrazine monohydrate (15 mL, 0.31 mol) is added and the mixture heated at reflux for 2 hours. The THF (top layer) is decanted and retained. The remaining mixture is extracted with $CH_2Cl_2$ (2×50 mL) and the organics combined. The THF/ $CH_2Cl_2$ solution is dried ($Na_2SO_4$), filtered and solvent evaporated. The residue is chromatographed on silica gel using 0–2% MeOH/$CH_2Cl_2$ eluant to obtain a yellow solid. The solid is dissolved in MeOH (20 mL) and Sodium Borohydride (0.22 g, 5.7 mmol) added at 0° C. The mixture is allowed to warm to room temperature and stirred 5 hours. Solvent is evaporated to obtain a purple solid. This material is added to dry THF (30 mL) and $NaHCO_3$ (0.46 g, 5.3 mmol) added. Benzyl chloroformate (0.76 mL, 5.3 mmol) is added dropwise and the mixture allowed to warm to room temperature while stirring overnight. The mixture is partitioned between water and EtOAc. The organic layer is washed with water then brine and dried ($Na_2SO_4$). Solvent is evaporated and the residue chromatographed on silica gel using 25% EtOAc/Heptane eluant. The oily product is triturated with heptane to give an off-white solid (51%); mp104–106° C. MS (EI) m/z 432 ($M^+$), Anal. Calcd for $C_{25}H_{24}N_2O_5$: C, 69.43; H, 5.59; N, 6.48. Found: C, 69.21; H, 5.74; N, 6.49.

Step 5 Preparation of benzyl 7-[(5R)-5-(hydroxymethyl)-2-oxo-1,3-oxazolidin-3-yl]-3-methyl-2,3-dihydro-4H-1,4-benzoxazine-4-carboxylate Following the procedure described in EXAMPLE 1, Step 4, but using the product of the above step as a starting material, the title compound is obtained. The title compound is purified by chromatography on silica gel using 0–3% MeOH/$CH_2Cl_2$ gradient gave product as an off-white foamy solid (65%); mp 68–73° C.(decomp); HRMS (FAB) calcd for $C_{21}H_{22}N_2O_6+H_1$ 399.1556, found 399.1578.

Step 6 Preparation of benzyl 7-{(5S)-5-[(acetylamino)methyl]-2-oxo-1,3-oxazolidin-3-yl}-3-methyl-2,3-dihydro-4H-1,4-benzoxazine-4-carboxylate Following the procedure described in EXAMPLE 13, Step 4, but using the product of the above step as a starting material, the title compound is obtained. The title compound is isolated as a white solid (66%); mp 78–81° C. HRMS (EI) calcd for $C_{23}H_{25}N_3O_6$ 439.1743, found 439.1737. $[\alpha]^{25}_D$=–19° (c 0.88, DMSO).

Step 7 Preparation of N-{[(5S)-3-(3-methyl-3,4-dihydro-2H-1,4-benzoxazin-7-yl)-2-oxo-1,3-oxazolidin-5-yl]methyl}acetamide Following the procedure described in EXAMPLE 13, Step 5, but using the product of the above step as a starting material, the title compound is obtained. The title compound is isolated as an off-white solid(72%); mp163–165° C. HRMS (FAB) calcd for $C_{15}H_{19}N_3O_4+H_1$ 306.1454, found 306.1433.

Step 8 Preparation of N-{[(5S)-3-(4-Formyl-3-methyl-3,4-dihydro-2H-1,4-benzoxazin-7-yl)-2-oxo-1,3-oxazolidin-5-yl]methyl}acetamide Following the procedure described in EXAMPLE 13, Step 6, but using the product of the above step as a starting material, the title compound is obtained. The title compound is isolated as a white solid (97%); mp 118–121° C. (decomp). HRMS (FAB) calcd for $C_{16}H_{19}N_3O_5+H_1$ 334.1403, found 334.1382.

EXAMPLE 17

N-({(5S)-3-[(3R)-4-Formyl-3-methyl-3,4-dihydro-2H-1,4-benzoxazin-7-yl]-2-oxo-1,3-oxazolidin-5-yl}methyl)acetamide

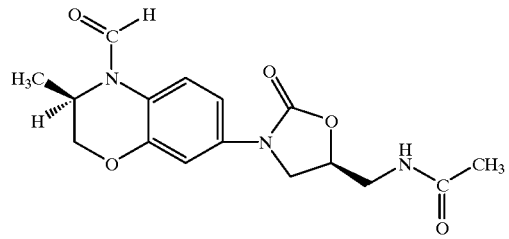

Step 1 Preparation of benzyl (3R)-7-[(5R)-5-(hydroxymethyl)-2-oxo-1,3-oxazolidin-3-yl]-3-methyl-2,3-dihydro-4H-4-benzoxazine-4-carboxylate The product of Example 16, Step 5 is seperated into its component diastereomers by preperative liquid chromatography using a 5×50 cm Chiralcell® OJ column at 35° C. eluting with EtOH (0.4 mL/min). The first eluting fraction is collected, solvent is removed by evaporation and the resulting solid recrystallized from MeOAc/Heptane. Absolute stereochemistry is determined by X-ray crystallography; mp143–145° C. MS (EI) m/z 398 ($M^+$); Anal. Calcd for $C_{21}H_{22}N_2O_6$: C, 63.31; H, 5.57; N, 7.03. Found: C, 63.22; H, 5.80; N, 6.93.

Also, the above second eluting fraction is collected, solvent is removed by evaporation and the resulting solid recrystallized from MeOAc/Heptane. Absolute stereochemistry is determined by X-ray crystallography as benzyl (3S)-7-[(5R)-5-(hydroxymethyl)-2-oxo-1,3-oxazolidin-3-yl]-3-methyl-2,3-dihydro-4H-1,4-benzoxazine-4-carboxylate; mp143–5° C. MS (EI) m/z 398 ($M^+$); Anal. Calcd for $C_{21}H_{22}N_2O_6$: C, 63.31; H, 5.57; N, 7.03. Found: C, 63.20; H, 5.68; N, 7.00.

Step 2 Preparation of benzyl (3R)-7-{(5S)-5-[(acetylamino)methyl]-2-oxo-1,3-oxazolidin-3-yl}-3-methyl-2,3-dihydro-4H-1,4-benzoxazine-4-carboxylate Following the procedure described in EXAMPLE 13, Step 4, but using benzyl (3R)-7-[(5R)-5-(hydroxymethyl)-2-oxo-1,3-oxazolidin-3-yl]-3-methyl-2,3-dihydro-4H-1,4-benzoxazine-4-carboxylate as a starting material, the title compound is obtained. Product is isolated as an off-white solid (70%); mp 79–82° C. HRMS (FAB) calcd for $C_{23}H_{25}N_3O_6+H_1$ 440.1821, found 440.1819.

Step3 Preparation of N-({(5S)-3-[(3R)-4-formyl-3-methyl-3,4-dihydro-2H-1,4-benzoxazin-7-yl]-2-oxo-1,3-oxazolidin-5-yl}methyl)acetamide Following the procedure described in EXAMPLE 13, Step 5, but using the above product as a starting material to give the deprotected intermediate. This intermediate is reacted according to the produce described in EXAMPLE 14, Step 3 to provide the title compound. Product is isolated as a white solid (80%); mp 148–151° C.; $[\alpha]^{25}_D$=–75°

(DMSO). HRMS (FAB) calcd for $C_{16}H_{19}N_3O_5+H_1$ 334.1403, found 334.1398.

EXAMPLE 18

N-({(5S)-3-[(3R)-4-Formyl-3-methyl-3,4-dihydro-2H-1,4-benzoxazin-7yl]-2-oxo-1,3-oxazolidin-5-yl}methyl)ethanethioamide

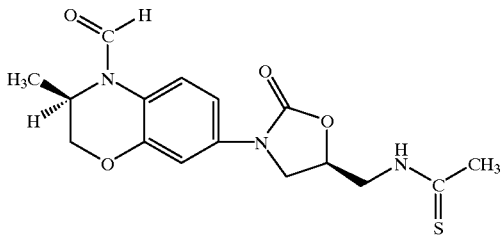

Step 1 Preparation of benzyl (3R)-7-{(5S)-5-[(ethanethioylamino)methyl]-2-oxo-1,3-oxazolidin-3-yl}-3-methyl-2,3-dihydro-4H-1,4-benzoxazine-4-carboxylate Following the procedure described in EXAMPLE 15, Step 1, but using the product of EXAMPLE 17, Step 2 (0.5 g, 1.1 mmol) as a starting material, the title compound is obtained as an off-white solid (81%); mp 84–86° C. HRMS (FAB) calcd for $C_{23}H_{25}N_3O_5S+H_1$ 456.1593, found 456.1601.

Step 2 Preparation of N-({(5S)-3-[(3R)-3-Methyl-3,4-dihydro-2H-1,4-benzoxazin-7-yl]-2-oxo-1,3-oxazolidin-5-yl}-methyl)ethanethioamide The above product (0.41 g, 0.9 mmol) is dissolved in Acetic Acid (10 mL). 30% HBr/Acetic Acid (10 mL) is added dropwise and the mixture stirred 1 hour. $Et_2O$ (200 mL) is added to precipitate the intermediate amine as a salt. The $Et_2O$ is decanted and $Et_2O$ (200 mL) added again to wash. The $Et_2O$ is decanted and $H_2O$(50 mL) added to dissolve the solid. The aqueous solution is made basic with saturated $NaHCO_3$. The product is extracted into $CH_2Cl_2$ (2×50 mL). The organics are dried ($Na_2SO_4$), filtered and solvent evaporated. Chromatography on silica using MeOH/$CH_2Cl_2$ (0–3% gradient) eluant gave product as a white solid (69%); mp 74–77° C.

Step 3 Preparation of N-({(5S)-3-[(3R)-4-formyl-3-methyl-3,4-dihydro-2H-1,4-benzoxazin-7-yl]-2-oxo-1,3-oxazolidin-5-yl}methyl)ethanethioamide Following the procedure described in EXAMPLE 14, Step 3, but using the above product as a starting material, the title compound is obtained. The title compound is isolated as a solid (99%); mp 95–8° C.; $[\alpha]^{25}_D=-42°$(DMSO). HRMS (FAB) calcd for $C_{16}H_{19}N_3O_4S+H_1$ 350.1174, found 350.1188.

EXAMPLE 19

(S)-N-[[3-[1-Formyl-2-(fluoromethyl)-5-indolinyl]-2-oxo-5-oxazolidinyl]methyl]acetamide

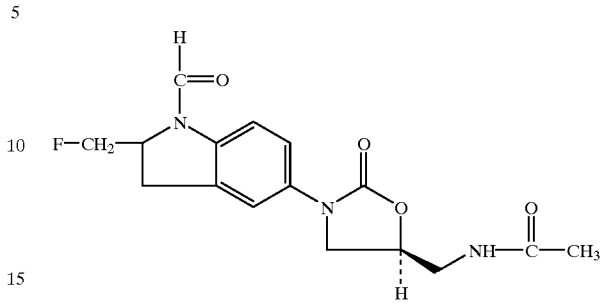

Step 1 Preparation of ethyl 5-aminoindol-2-carboxylate

A mixture of ethyl 5-nitro-1H-indole-2-carboxylate (15.0 g, 0.0641 mol), 10% palladium-on-carbon catalyst, ethanol (300 ml) and tetrahydrofuran (300 ml) is hydrogenated at an initial pressure of 47 p.s.i. for 9 h and filtered through celite. The filtrate is concentrated and the residue is digested with hot diethyl ether. Concentration of the ether extract gave the titled product (11.14 g): MS (ES) m/z 205 (M+H⁺), 227 (M+Na⁺). *Uhlig, F.; Snyder, H. R. *Adv. Org. Chem.* 1960, 1, 35; Parmerter, S. M.; Cook, A. G.; Dixon, W. B. *J. Am. Chem. Soc.* 1958, 80, 4621–2.

Step 2 Preparation of methyl 5-aminoindolin-2-carboxylate

A stirred solution of the product from Step 1 (8.81 g, 0.0431 mol), under nitrogen, is treated with magnesium turnings (3.3 g) and kept for about 10 min when the solution became cloudy and an exothermic reaction began. It is stirred for an additional 5 min (23–24° C.), cooled to 6–7° C. in a water bath and kept for 5.5 h. This mixture is kept at 8° C. for 18 h, acidified to pH 3 with ice cold 6N HCl, neutralized with saturated $NaHCO_3$, and extracted with EtOAc. The extracts are washed with water, dried ($Na_2SO_4$) and concentrated in vacuo to give 7.39 g of the titled product: MS (ES) m/z 193 (M+H⁺), 215 (17+Na⁺); ¹H NMR (300 MHz, $CDCl_3$); δ3.28 (m, 2H), 3.52 (broad s, 3H), 374 (s, 3H), 4.33 (q, 1H), 6.46 (m, 1H), 6.56 (m, 2H).

Step 3 Preparation of methyl 5-benzyloxycarbonylamino-1-benzyloxycarbonylindolin-2-carboxylate A stirred mixture of the product from Step 2 (7.39 g, 0.0044 mol), acetone (130 ml), water (130 ml) and $NaHCO_3$ (12 g, 0.143 mol) is cooled, under nitrogen in an ice bath and treated, dropwise stirring 10 min, with benzyl chloroformate (14.42 ml). It is kept in the ice bath for 20 min and at ambient temperature for 3.5 h and concentrated to remove acetone. The resulting solid is collected by filtration, washed with water, dried and recrystallized from EtOAc (Darco) to give 8.23 g of the titled product.

Step 4 Preparation of 5-benzyloxycarbonylamino-1-benzyloxycarbonylindolin-2-carbanol A stirred, ice cold solution of the product from Step 3 (3.06 g, 0.00665 mol) in tetrahydrofuran (25 ml) is treated, portionwise during 5 min, with lithium borohydride (0.53 g, 0.0241 mol). The mixture is warmed to ambient temperature during 90 min and kept for 18 h. It is then cooled in an ice bath, mixed with ice water, treated dropwise with acetic acid (1 ml) and extracted with EtOAc. The extracts are washed with water and brine, dried (MgSO$_4$) and concentrated. Crystallization of the residue from acetone-heptane gave 1.75 g of the titled product: MS (ES) m/z 433 (M+H$^+$), 455 (M+Na$^+$); $^1$H NMR (300 MHz, CDCl$_3$); δ1.75 (broad s), 2.88 (broad s, 1H), 3.30 (q, 1H), 3.73 (s, 2H), 4.63 (broad s, 1H), 5.17 (s, 2H), 5.28 (s, 2H), 6.64 (s, 1H), 6.99 (m, 1H), 7.36 (m, 11H), 7.67 (broad s, 1H).

Step 5 Preparation of 5-benzyloxycarbonylamino-1-benzyloxycarbonyl-2-[(tert-butyldimethylsilyl)oxy]-methylindoline A stirred mixture of the product from Step 4 (9.2 g, 0.021 mol), imidazole (4.19 g, 0.0615 mol) and dimethylformamide (50 ml) is treated with tert-butyldimethylsilyl chloride (4.83 g, 0.0320 mol), kept at ambient temperature for 18 h, concentrated to about 20 ml in vacuo and poured into ice water. This mixture is extracted with Et$_2$O. The extracts are washed with water and brine, dried (MgSO$_4$) and concentrated. Chromatography of the residue on silica gel with mixtures of CHCl$_3$ and CH$_2$Cl$_2$ containing 100% CHCl$_3$ to 100% CH$_2$Cl$_2$ gave 8.32 g of the titled product: MS (ES) mnz 547 (M+H$^+$), 569 (M+Na$^+$); $^1$H NMR (300 MHz, CDCl$_3$) δ−0.10 (s, 3H), −0.06 (s, 3H), 0.76 (s, 9H), 3.07 (m, 1H), 3.21 (m, 1H), 3.51 (broad s, 1H), 3.76 (broad s, 1H), 4.50 (broad s, 1H), 5.19 (s, 2H), 5.27 (broad s, 2H), 6.54 (s, 1H), 6.98 (d, 1H), 7.38 (m, 11H), 7.72 (broad s, 1H).

Step 6 Preparation of (S)-[3-[1-benzyloxycarbonyl-2-[[(tert-butyldimethylsilyl)oxy]methyl]-5-indolinyl]-5-hydroxymethyloxazolidin-2-one A stirred mixture of the product from Step 5 (1.5 g, 0.0027 mol) and tetrahydrofuran (40 ml) is cooled, under nitrogen to −70° C. and treated dropwise stirring 2 min, with 1.6 M n-butyl lithium in hexane (1.76 ml). It is kept at −70° C. for 30 min and then treated with (R)(−)-glycidyl butyrate (0.393 ml, 0.00278 mol). This mixture is allowed to warm slowly to ambient temperature and stand for 20 h. It is then diluted with EtOAc, washed with cold, dilute NH$_4$Cl, water and brine, dried (MgSO$_4$) and concentrated. Chromatography of the residue on silica gel with mixtures of MeOH—CH$_2$Cl$_2$ containing 1–2% MeOH gave 0.96 g of the titled product: MS (ES) m/z 513 (M+H$^+$), 535 (M+Na$^+$).

Step 7 Preparation of (S)-[3-[1-Benzyloxycarbonyl-2-[[(tert-butyldimethylsilyl)oxy]methyl]-5-indolinyl]-5-aminomethyloxazolidin-2-one An ice cold, stirred mixture of the product from Step 6 (6.03 g, 0.0117 mol) and triethylamine (4.55 ml) in methylene chloride (340 ml) is treated, portionwise during 10 min, with 3-nitrobenzenesulfonyl chloride (3.2 g) and kept in the ice bath for 15 min. It is then kept at ambient temperature for 16 h, diluted with CH$_2$Cl$_2$, washed with saturated NaHCO$_3$ and brine, dried (MgSO$_4$) and concentrated. A stirred solution of the residue (9.32 g) in a mixture of 2-propanol (250 ml), acetonitrile (250 ml), and concentrated ammonium hydroxide (250 ml) is warmed at 55° C. under a dry ice-acetone condenser for 3.5 h and kept at ambient temperature for 18 h. Additional ammonium hydroxide (50 ml) is added; the mixture is warmed at 55° C. for 30 min, kept at ambient temperature for 3 d and concentrated in vacuo. The aqueous residue is extracted with methylene chloride. The extract is washed water and brine, dried (Na$_2$SO$_4$) and concentrated to give 6.53 g of the titled product: $^1$H NMR (300 MHz, CDCl$_3$) δ−0.11 (s, 3H), −0.06 (s, 3H), 0.76 (s, 9H), 3.03 (m, 3H), 3.24 (m, 1H), 3.79 (m, 2H), 4.02 (m, 2H), 4.52 (broad s, 1H), 4.65 (m, 1H), 5.27 (m, 2H), 7.08 (m, 1H), 7.38 (m, 5H), 7.62, 7.79 (broad s, 2H).

Step 8 Preparation of (S)-N-[[3-[1-Benzyloxycarbonyl-2-[[(tert-butyldimethylsilyl)oxy]methyl]-5-indolinyl]-2-oxo-5-oxazolidinyl]methyl]acetamide An ice cold, stirred mixture of the product from Step 7 (6.39 g, 0.0125 mol) and pyridine (75 ml), under nitrogen is treated, dropwise during 10 min, with acetic anhydride (24 ml). The mixture is kept in the ice bath for 20 min and at ambient temperature for 2 h. It is then concentrated in vacuo. The residue is mixed with ethyl acetate, washed with dilute sodium bicarbonate, water, and brine, dried (Na$_2$SO$_4$) and concentrated. Chromatography of the residue on silica gel with mixtures of MeOH—CH$_2$Cl$_2$ containing 2.5 −5% MeOH gave the titled product: MS (ES) m/z 554 (M+H$^+$), 576 (M+Na$^+$); $^1$H NMR (300 MHz, CDCl$_3$) δ−0.12 (s, 3H), −0.07 (s, 3H), 0.75 (s, 9H), 2.01 (s, 3H), 3.08 (m, 1H), 3.23 (m, 1H), 3.58 (m, 2H), 3.73 (m, 3H), 4.00 (m, 1H), 4.50 (broad s, 1H), 4.73 (m, 1H), 5.27 (m, 2H), 6.22 (broad s, 1H), 7.08 (m, 1H), 7.37 (m, 6H), 7.79 (broad s, 1H).

Step 9 Preparation of (S)-N-[[3-[2-[[(tert-butyldimethylsilyl)oxy]methyl]-5-indolinyl]-2-oxo-5-oxazolidinyl]methyl]acetamide A mixture of the product from Step 8 (2.2 g, 0.0040 mol), 10% palladium-on-carbon catalyst (0.4 g) and ethanol (150 ml) is hydrogenated at an initial pressure of 44 p.s.i. for 2 h. The catalyst is removed by filtration through celite and the filtrate is concentrated. The residue is dissolved in CH$_2$Cl$_2$, filtered and concentrated to give the titled product: MS (ES) m/z 420 (M+H$^+$), 442 (M+Na$^+$); $^1$H NMR (300 MHz, CDCl$_3$) δ0.05 (s, 6H), 0.89 (s, 9H), 2.02 (s, 3H), 2.63 (q, 1H), 3.09 (q, 1H), 3.53 (m, 3H), 3.71 (m, 2H), 4.23 (broad s, 1H), 4.71 (m, 1H), 6.14 (t, 1H), 6.58 (d, 1H), 6.98 (d, d, 1H), 7.26 (d, 1H).

Step 10 Preparation of (S)-N-[[3-[2-[[(tert-butyldimethylsilyl)oxy]methyl]-1-formyl-5-indolinyl]-2-oxo-5-oxazolidinyl]methyl]acetamide A stirred mixture of the product from Step 9 (0.39 g, 0.93 mmol) and THF (15 ml), under nitrogen is treated with N-formylbenzotriazole (0.164 g, 1.12 mmol) and kept at ambient temperature for 1 h. It is then concentrated in vacuo. Chromatography of the residue on silica gel with mixtures of acetone-methylene chloride containing 20–40% acetone gave 0.37 g of the titled product: $^1$H NMR (300 MHz, CDCl$_3$) δ0.00 (m, 6H), 0.73, 0.86 (s, s, 9H), 2.02 (s, 3H), 2.70, 3.23 (m, m, 2H), 3.68 (m, 5H), 4.03 (m, 1H), 4.43, 4.80 (m, m, 1H), 4.75 (m, 1H), 6.14 (m, 1H), 7.08, 7.20, 7.47, 7.61, 8.04 (m, 3H), 8.52, 8.86 (s, s, 1H).

Step 11 (S)-N-[[3-[2-(Hydroxymethyl)-1-formyl-5-indolinyl]-2-oxo-5-oxazolidinyl]-methyl]acetamide A stirred, ice cold mixture of the product from Step 10 (0.35 g, 0.78 mmol) and THF (20 ml), under nitrogen is treated, dropwise stirring 3 min, with 1 M tetrabutylammonium fluoride in THF (3.31 ml). It is kept in the ice bath for 5 min and at ambient temperature for 2 h. It is then diluted with EtOAc, washed with water and brine, dried (MgSO$_4$) and concentrated. Chromatography of the residue over silica gel with acetone gave 0.20 g of the titled product: mp 132–136° C.; HRMS (FAB) calcd for $C_{16}H_{19}N_3O_5$+H 334.1403, found 334.1418; $^1$H NMR [300 MHz, $(CD_3)_2SO$] δ1.81 (s, 3H), 2.80, 3.01 (m, m, 1H), 3.38 (m, 5H), 3.69 (m, 1H), 4.06 (m, 1H), 4.45 (m, 1H), 4.68 (m, 1H), 4.89, 5.17 (t, t, 1H), 7.26 (m, 1H), 7.38, 7.86 (d, d, 1H), 7.48 (m, 1H), 8.24 (t, 1H), 8.44, 8.95 (s, s, 1H).

Step 12 (S)-N-[[3-[2-(Fluoromethyl)-1-formyl-5-indolinyl]-2-oxo-5-oxazolidinyl]-methyl]acetamide A stirred mixture of the product from Step 11 (0.085 g, 0.255 mmol)) and $CH_2Cl_2$ (10 ml), under nitrogen is cooled to −70° C. and treated, dropwise stirring 2 min, with a solution of (diethylamino)sulfur trifluoride (0.07 ml, 0.53 mmol) in $CH_2Cl_2$ (1 ml). The mixture is allowed to warm to ambient temperature slowly during 3 h. Additional $CH_2Cl_2$ (10 ml) is added and the mixture is kept at ambient temperature for 20 h, cooled to −70° C. and treated with 0.07 ml of additional DAST. It is kept at −70° C. for 1 h and at ambient temperature for 4 h, mixed with ice cold, saturated $NaHCO_3$ and extracted with EtOAc. The extracts are washed with water and brine, dried ($MgSO_4$) and concentrated. Chromatography of the residue on silica gel with 3.5% MeOH—$CH_2Cl_2$ gave 0.036 g of the titled product: HRMS (FAB) calcd for $C_{16}H_{18}FN_3O_4$+H 336.1359, found 336.1351; $^1$H NMR [300 MHz, $(CD_3)_2SO$] δ1.81 (s, 3H), 2.85, 3.00 (m, m, 1H), 3.38 (m, 3H), 3.71 (m, 1H), 4.06 (m, 1H), 4.30–4.88 (m, 4H), 7.30 (m, 1H), 7.43, 7.87 (d, d, 1H), 7.50 (m, 1H), 8.23 (t, 1H), 8.45, 9.00 (s, s, 1H).

EXAMPLE 20

N-{[(5R)-3-(2(+)-methyl-2,3-dihydro-1-benzothien-5-yl)-2-oxo-1,3-oxazolidin-5-yl]methyl}acetamide

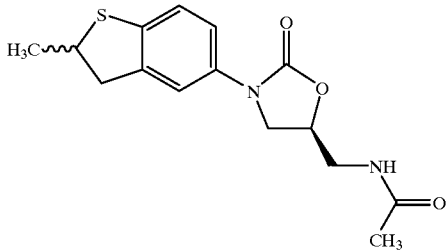

Step 1 Preparation of 5-nitrobenzo[b]thiophene

Methyl thioglycolate (14.3 g, 135 mmol) in methanol (250 mL) at 40° C. is treated dropwise with 25% sodium methoxide in methanol (37 mL, 160 mmol) and the resulting mixture mechanically stirred at 50° C. for 30 min. 2-chloro-5-nitrobenzaldehyde in methanol (250 mL) is added in a steady stream to give a heavy precipitate which is heated at 50° C. for 1 h. Sodium hydroxide (50% aqueous, 15 mL) is added and heating continued for 2 h, then cooled to ice bath temperature and acidified with concentrated hydrochloric acid. An additional 200 mL of water is added during this process to facilitate stirring. The resulting solids are collected by filtration, washed with water, and dried in vacuo at 45° C. overnight. The dried solids are suspended in quinoline (120 mL), copper metal (7.2 g) is added and the mixture is heated at 190° C. for 2 hr. The mixture is allowed to cool, then poured onto 500 g of ice, 6 N hydrochloric acid (500 mL) is added and then extracted with of dichloromethane. The organic layers are combined and washed with 6 N hydrochloric acid, dried, and flash chromatographed on silica gel eluting with 10–40% ethyl acetate in heptane to give 16.2 g (81%) of the title compound. $^1$H NMR ($CDCl_3$) δ8.75 (s, 1 H), 8.22 (dd, J=2.3, 10 Hz, 1 H), 8.0 (d, J=10 Hz, 1 H), 7.68 (d, J=6 Hz, 1 H), 7.53 (d, J=6 Hz, 1 H); MS (−ESI) m/z 221.8 (M−H)

Step 2 Preparation of 5-nitrobenzo[b]thiophene-1-dioxide

A mixture of 5-nitrobenzo[b]thiophene (16 g, 89 mmol) 30% hydrogen peroxide (70 mL) in acetic acid (300 mL) is heated on a steam bath for 3 h, then poured onto 500 g of ice. The mixture is diluted with 600 mL of water and the resulting solids collected by filtration, washed with water, and dried in vacuo to give 15.2 g (82%) of the title compound. $^1$H NMR ($CDCl_3$) δ8.45 (dd, J=2.0, 9.0 Hz, 1 H), 8.25 (d, J=2.0 Hz, 1 H), 7.92 (d, J=9.3 Hz, 1 H), 7.35 (d, J=8.3 Hz, 1 H), 6.94 (d, J=8.0 Hz, 1 H); MS (−ESI) m/z 211.0 (M−H)

Step 3 Preparation of 5-(2,3-dihydro-1-dioxido-benzo[b]thiophene)-2,5-dimethyl-1H-pyrrole A mixture of 5-nitrobenzo[b]thiophene-1-dioxide (15.2 g, 72 mmol) and 10% palladium on carbon (1.5 g) in ethanol (300 mL) is hydrogenated with shaking at 30 psi for 16 h, filtered through celite, and the filter cake washed 3×100 mL of methanol. The combined filtrates are concentrated by rotary evaporation and the resulting solid suspended in toluene (400 mL). 2,5-Hexanedione (9.5 mL, 79 mmol) and p-toluenesulfonic acid monohydrate (100 mg) are added and the solution refluxed for 18 hr with removal of water in a Dean-Stark trap. The solution is cooled, washed with aqueous bicarbonate, brine, dried, and flash chromatographed on silica gel eluting with 30% ethyl acetate in heptane to 14.1 g (75%) of the title compound. Anal. Calcd for $C_{14}H_{15}NO_2S$: C, 64.34; H, 5.78; N, 5.36; Found: C, 64.43; H, 5.85; N, 5.37; MS (+ESI) m/z 262.0 (M+H)

Step 4 Preparation of 5-(2-methyl-2,3-dihydro-1-dioxido-benzo[b]thiophene)-2,5-dimethyl-1H-pyrrole 5-(2,3-dihydro-1-dioxido-benzo[b]thiophene)-2,5-dimethyl-1H-pyrrole (9.68 g, 37 mmol) in dry tetrahydrofuran (350 mL) is cooled to −70° C. then treated dropwise with lithium bis(trimethylsilyl)amide (1 M in THF, 39 mL). The solution is stirred 30 min before adding iodomethane (3.5 mL, 55 mmol) and the solution allowed to warm to room temperature while stirring overnight. The solution is diluted with ethyl acetate (250 mL), washed with water and brine, dried and flash chromatographed on silica gel eluting with 25–30% ethyl acetate in heptane to give 7.42 g (73%) of the title compound. Anal. Calcd for $C_{15}H_{17}NO_2S$: C, 65.43; H, 6.22; N, 5.09. Found: C, 65.22; H, 6.30; N, 5.06; MS (+ESI m/z 276.1 (M+H)

Step 5 Preparation of 5-{[(benzyloxy)carbonyl]amino}-2-methyl-2,3-dihydrobenzo[b]thiophene Lithium aluminum hydride (1.1 g, 29 mmol) in diethyl ether (50 mL) is treated dropwise with 5-(2-methyl-2,3-dihydro-1-dioxido-benzo[b]thiophene)-2,5-dimethyl-1H-pyrrole (3.00 g, 11 mmol) in 1:1 THF/diethyl ether (100 mL) at room temperature over 15–20 min. The mixture is stirred for 18–20 h, carefully quenched with 1.1 mL of water followed by 1.1 mL of 2 N aqueous sodium hydroxide and 3.3 mL of water. The resulting suspension is filtered through celite and the filter cake is washed with THF and the combined filtrates concentrated via rotary evaporation. The resulting oil is dissolved in ethanol (50 mL) and hydroxylamine hydrochloride (6.9 g, 99 mmol) and triethylamine (2.8 mL, 20 mmol) are added and the solution refluxed overnight. After cooling, the mixture is diluted with water (200 mL), extracted with dichloromethane, dried and concentrated. The resulting oil is dissolved in acetone (50 mL) and water (15 mL), treated with sodium bicarbonate (5.0 g, 36 mmol) and benzyl chloroformate (2.5 mL, 17.6 mmol) and stirred overnight. The acetone is removed via rotary evaporation then the mixture is diluted with water, extracted with dichloromethane, dried, and flash chromatographed on silica gel eluting with 10% ethyl acetate in heptane to give 2.25 g (69%) of the title compound. Anal. Calcd for $C_{17}H_{17}NO_2S$: C, 68.20; H, 5.72; N, 4.68. Found: C, 68.21; H, 5.82; N, 4.67; MS (+ESI) m/z 300.1 (M+H).

Step 6 Preparation of N-{[(5S)-3-[2(−)-methyl-2,3-dihydro-1-benzothien-5-yl]-2-oxo-1,3-oxazolidin-5-yl]methyl}acetamide and N-{[(5S)-3-[2(+)-methyl-2,3-dihydro-1-benzothien-5-yl]-2-oxo-1,3-oxazolidin-5-yl]methyl}acetamide To a 15° C. suspension of 5-{[(benzyloxy)carbonyl]amino}-2-methyl-2,3-dihydrobenzo[b]thiophene (1.5 g, 5 mmol) in dimethylformamide (3 mL) is added methanol (406 µL, 10 mmol) and then 1M lithium-t-butoxide in hexanes (15 mL, 15 mmol) dropwise over 2 h. The mixture is cooled to 5° C. and (1S)-2-(acetylamino)-1-(chloromethyl)ethyl acetate (1.94 g, 10 mmol) is added in one portion. Stirring is continued overnight at room temperature when saturated aqueous ammonium chloride (50 mL) is added and then extracted with dichloromethane, dried, and flash chromatographed on silica gel eluting with 5% methanol in dichloromethane to give 1.20 (78%) of a mixture of the title compounds. The title compounds are resolved on a Chiralpak AD column eluting with ethanol to give the 2-(−)-isomer ($[\alpha]^{25}_D$=−102 (c 0.49, DMSO). Anal. Calcd for $C_{15}H_{18}N_2O_3S$: C, 58.80; H, 5.92; N, 9.14. Found: C, 59.03; H, 6.03; N, 8.99) and the 2-(+)-isomer ($[\alpha]^{25}_D$=55 (c 0.58, DMSO). Anal. Calcd for $C_{15}H_{18}N_2O_3S$: C, 58.80; H, 5.92; N, 9.14. Found: C, 59.12; H, 6.09; N, 8.78.)

EXAMPLE 21

N-[[(5S)-3-[2-(1,1-dimethylethyl)-1-formyl-2,3-dihydro-1H-indol-5-yl]-2-oxo-5-oxazolidinyl]methyl]ethanethioamide

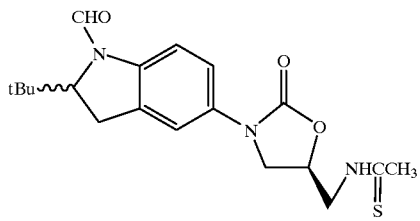

Step 1 Preparation of 1-acetyl-2-t-butylindoline 2-t-Butylindoline (20.3 g, 116 mmol) (can be made according to the procedures described in J. Chem Soc. Chem. Commum. 1974, 677–678) and 4-dimethylaminopyridine (10 mg) are dissolved in pyridine (100 ml). Acetic anhydride (11.5 ml, 122 mmol) is added and the solution stirred for 2 hours. The mixture is poured into water (1 L) and the solid filtered and dried in vacuo. The title compound is obtained as white crystals (22.2 g, 88%): mp 75° C.

Step 2 Preparation of 1-acetyl-2-t-butyl-5-nitroindoline

Material from the previous step (22.2 g, 102 mmol) is dissolved in trifluoroacetic acid (100 ml). Sodium nitrate (8.71 g, 102 mmol) is added over 10 minutes and the reaction stirred for 4 hours. Ice-water (1 L) is added and the mixture treated with solid sodium hydroxide (40 g, 1 mole) with cooling. The mixture is extracted with ether (2×500 ml), backwashed with brine (100 ml) and dried ($MgSO_4$). Evaporation gave a dark red oil which is dissolved in ethanol (50 ml) and placed in a freezer overnight. The resultant crystals are filtered to afford the nitro compound as golden granules (15.0 g, 56%) mp 99° C.

Step 3 Preparation of 2-t-butyl-5-nitroindoline

Nitroamide prepared in the previous step (14.5 g, 55.3 mmol) is heated under reflux in a mixture of ethanol (100 ml) and 5N.HCl (150 ml) for 2 hours. Upon cooling, water (1.5 L) is added and the solid filtered. The product is obtained as a yellow solid (11.5 g, 94%): mp 110–112° C.

Step 4 Preparation of phenylmethyl 2-(1,1-dimethylethyl)-2,3-dihydro-5-[[(phenylmethoxy)carbonyl]amino]-1H-indole-1-carboxylate The nitroindoline from the previous step (9.0 g, 40.9 mmol) is dissolved in a mixture of ethyl acetate (125 ml) and ethanol (125 ml) and hydrogenated at 30 psi in the presence of 10% Pd/C (1.6 g) for 2 hours. Filtration through cellulose and evaporation gave crude 5-aminoindoline (7.77 g, 100%) as a brown oil which is dissolved in THF (180 ml). To this solution is added a solution of $NaHCO_3$ (14.4 g, 171.4 mmol) in water (180 ml) followed by benzyl chloroformate (14.4 ml, 100.8 mmol). The reaction is stirred for 30 minutes then most of the THF evaporated. Ethyl acetate (500 ml) is added and the organic layer washed with brine (100 ml) and dried ($MgSO_4$). Evaporation gave a gum which is chromatographed over silica gel (500 g) eluting with 10–20% ethyl acetate-hexane. The product is obtained as a white foam (18.5 g, 99%). MS (electrospray) m/z 459 (m+1). Anal: Calcd. for $C_{28}H_{30}N_2O_4$: C, 73.34; H, 6.59; N, 6.11. Found: C, 73.04; H, 6.71; N, 5.99.

Step 5 Preparation of phenylmethyl 2-(1,1-dimethylethyl)-2,3-dihydro-5-[(5R)-5-(hydroxymethyl)-2-oxo-3-oxazolidinyl]-1H-indole-1-carboxylate The compound from the previous step (19.77 g, 43.2 mmol) is dissolved in dry THF (150 ml) under nitrogen and cooled to −78°. A solution of 1.6 N.nBuLi in hexane (30 ml, 48 mmol) is added over 1 minute and stirred for 1 hour. A solution of R(−) glycidyl butyrate (7.0 g, 48.6 mmol) in dry THF (25 ml) is added over 3 minutes and the mixture allowed to warm to ambient temperature overnight. The solvent is evaporated and the residue partitioned between ethyl acetate (750 ml) and saturated $NH_4Cl$ solution (150 ml). The organic layer is washed with brine (100 ml) and dried ($MgSO_4$). Evaporation gave a yellow oil which is chromatographed over silica gel (500 g) eluting with 50–100% ethyl acetate-hexane. The product is obtained as a white solid (11.2 g, 61%): mp 141–149° C.

Step 6 Preparation of phenylmethyl 2-(1,1-dimethylethyl)-2,3-dihydro-5-[(5R)-5-[[(methylsulfonyl)oxy]methyl]-2-oxo-3-oxazolidinyl]-1H-indole-1-carboxylate The alcohol prepared in Step 5 (11.3 g, 26.6 mmol) is dissolved in $CH_2Cl_2$ (125 ml) with triethylamine (11.0 ml, 79 mmol) and cooled to 0°. Methanesulfonylchloride (2.4 ml, 31 mmol) is added and the reaction stirred for 2 hours. Extra $CH_2Cl_2$ (100 ml) is added and the solution washed with water (100 ml) and brine (50 ml) then dried ($MgSO_4$). Evaporation gave a gum which is chromatographed over silica gel (500 g) eluting with 25–60% ethyl acetate-hexane. The product is obtained as a white foam (10.95 g, 82%): HRMS (FAB): Calcd for m+Na=525.1672; Found: 525.1671. Anal: Calcd. for $C_{25}H_{30}N_2O_7S$: C, 59.74; H, 6.02; N, 5.57. Found: C, 59.44; H, 6.07; N, 5.49.

Step 7 Preparation of phenylmethyl 5-[(5R)-5-(azidomethyl)-2-oxo-3-oxazolidinyl]-2-(1,1-dimethylethyl)-2,3-dihydro-1H-indole-1-carboxylate A mixture of the mesylate from Step 6 (10.56 g, 21.0 mmol) and sodium azide (6.8 g, 104.6 mmol) in DMF (100 ml) is heated at 60° for 7 hours. The DMF is evaporated (45°/0.6 mm) and the residue partitioned between ethyl acetate (250 ml) and water (100 ml). The organic layer is washed with water (100 ml) and brine (50 ml), then dried ($MgSO_4$). Evaporation yielded the product (9.0 g, 95%) as a glassy foam: Anal: Calcd. for $C_{24}H_{27}N_5O_4$: C, 64.13; H, 6.05; N, 15.58. Found: C, 63.84; H, 6.15; N, 15.23.

Step 8 Preparation of phenylmethyl 5-[(5S)-5-(aminomethyl)-2-oxo-3-oxazolidinyl]-2-(1,1-dimethylethyl)-2,3-dihydro-1H-indole-1-carboxylate A solution of the azide (8.68 g, 19.3 mmol) from the previous step, in dry THF (75 ml) is treated with triphenyl phosphine (5.77 g, 22.0 mmol). After 19 hours water (5 ml) is added and the reaction stirred for 24 hours. The solvents are evaporated and the residue chromatographed over silica gel (500 g) eluting with 1–10% methanol-chloroform. The amine is obtained as a white solid (7.51 g, 92%): mp 80–85° C. HRMS (FAB): Calcd. for m+H=424.2236; Found: 424.2229.

Step 9 Preparation of phenylmethyl 5-[(5S)-5-[[[(1,1-dimethylethoxy)carbonyl]amino]-methyl]-2-oxo-3-oxazolidinyl]-2-(1,1-dimethylethyl)-2,3-dihydro-1H-indole-1-carboxylate A solution of the amine (7.23 g, 17.1 mmol) from the previous step and di-t-butyl dicarbonate (3.84 g, 17.6 mmol) in THF (50 ml) is stirred for 2 hours. The solvent is evaporated and the residue chromatographed over silica gel (500 g) eluting with 1–5% methanol-chloroform. The product is obtained as a white foam (8.91 g, 100%). HRMS (FAB): Calcd. for m+Na=546.2580. Found: 546.2568.

Step 10 Preparation of 1,1-dimethylethyl[[(5S)-3-[2-(1,1-dimethylethyl)-2,3-dihydro-1H-indol-5-yl]-2-oxo-5-oxazolidinyl]methyl]carbamate Compound from the previous step (8.72 g, 16.7 mmol) is hydrogenated at 30 psi in ethyl acetate (125 ml) and ethanol (125 ml) in the presence of 10% Pd/C (1.0 g) for 16 hours. Filtration and evaporation gave a pale yellow solid (6.48 g, 100%): mp 153–160° C. HRMS (FAB): Calcd. for m+H=390.2393. Found: 390.2393.

Step 11 Preparation of 1,1-dimethylethyl[[(5S)-3-[2-(1,1-dimethylethyl)-1-formyl-2,3-dihydro-1H-indol-5-yl]-2-oxo-5-oxazolidinyl]methyl]carbamate The indoline from the previous step (2.0 g, 5.14 mmol) is stirred with N-formylbenzotriazole (1.0 g, 6.80 mmol) in THF (25 ml) for 24 hours. The solvent is evaporated and the residue chromatographed over silica gel (40 g) eluting with 25–75% ethyl acetate-hexane. The product is obtained as a white solid (1.88 g, 88%): mp 153–161° C. Anal: Calcd. for $C_{22}H_{31}N_3O_5$: C, 63.29; H, 7.48; N, 10.06. Found: C, 63.29; H, 7.57; N, 10.02.

Step 12 Preparation of 5-[(5S)-5-(aminomethyl)-2-oxo-3-oxazolidinyl]-2-(1,1-dimethylethyl)-2,3-dihydro-1H-indole-1-carboxaldehyde monohydrochloride The compound from the previous step (1.77 g, 4.24 mmol) is stirred in 4N.HCl in dioxane (40 ml) for 3 hours. Evaporation of the solvent gave the product as a pink solid (1.50 g, 100%): HRMS (FAB): Calcd. for m+H=318.1817. Found: 318.1803.

Step 13 Preparation of N-[[(5S)-3-[2-(1,1-dimethylethyl)-1-formyl-2,3-dihydro-1-H-indol-5-yl]-2-oxo-5-oxazolidinyl]methyl]ethanethioamide The amine hydrochloride salt (200 mg, 0.566 mmol) prepared in Step 12 is stirred in a mixture of methanol (4 ml) and triethylamine (0.234 ml, 1.683 mmol). To this solution is added ethyl dithioacetate (0.08 ml, 0.70 mmol) and the mixture heated to reflux for 2 hours then allowed to cool. The precipitate is filtered to afford the thioamide as white needles (97 mg, 46%): mp 219–221° C. Anal: Calcd. for $C_{19}H_{25}N_3O_3S$: C, 60.78; H, 6.71; N, 11.19. Found: C, 60.63; H, 6.80; N, 11.12.

Chart I
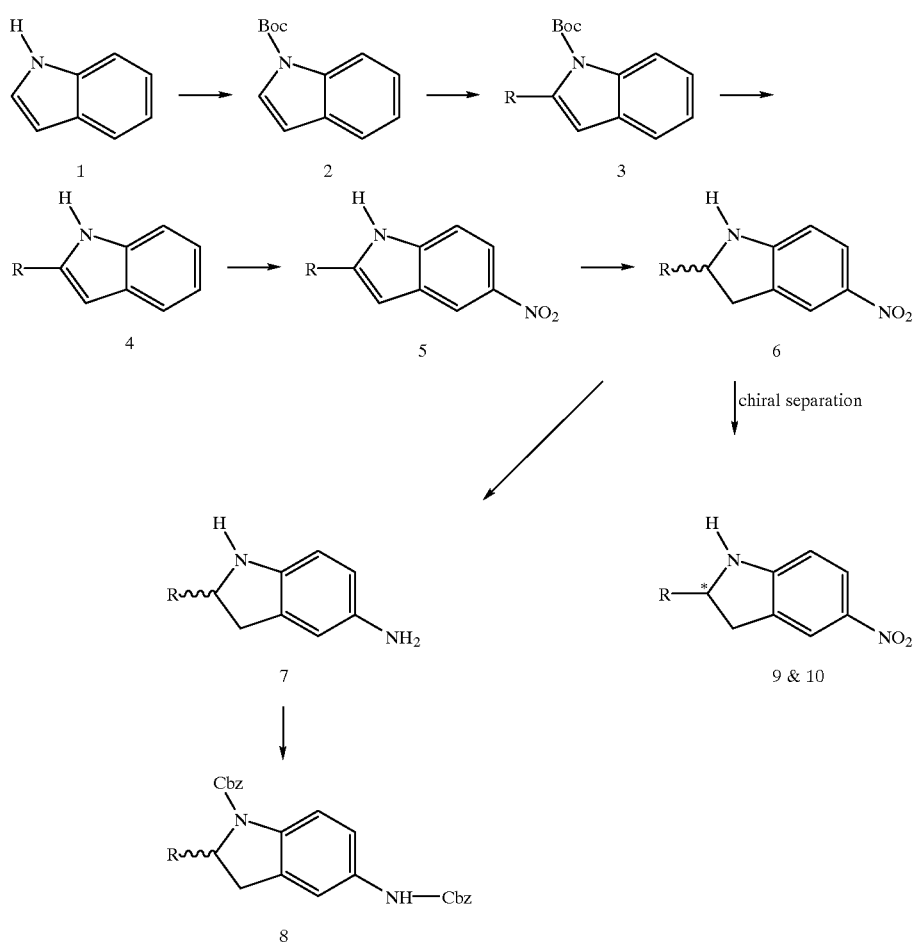
Chart II
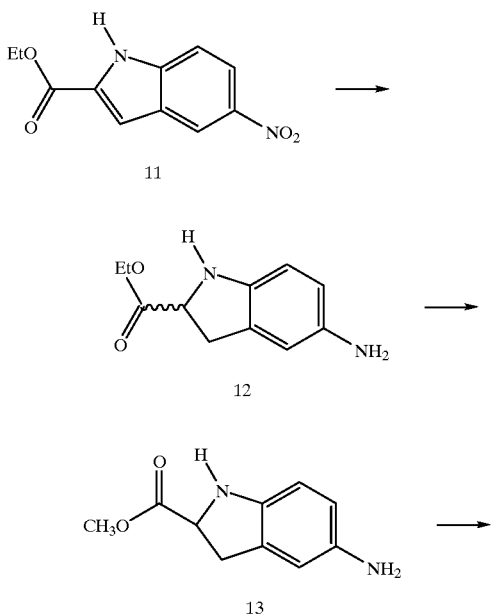
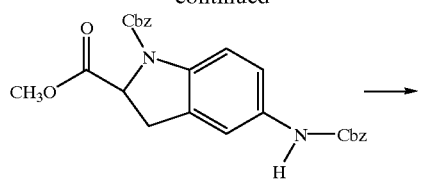
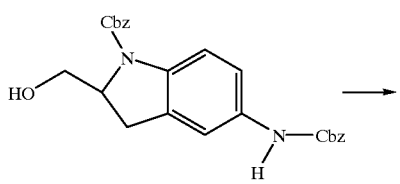
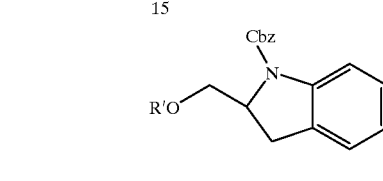
-continued

Chart III
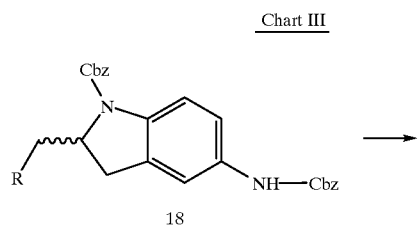
18
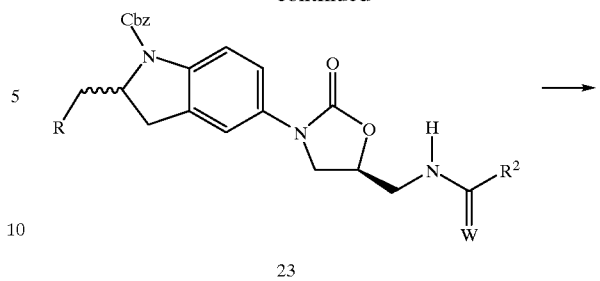
23
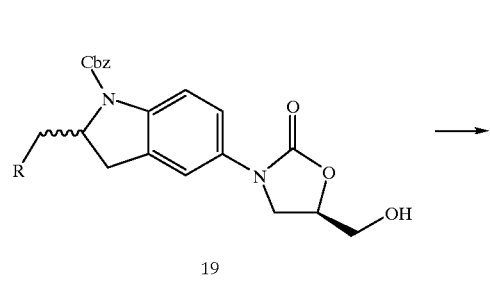
19
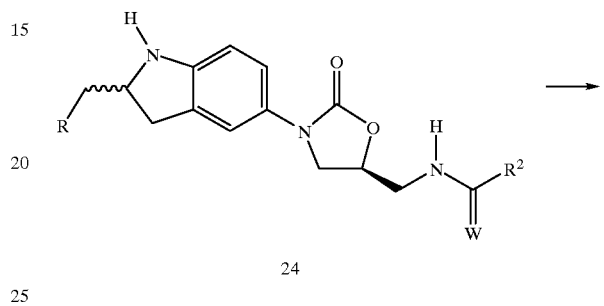
24
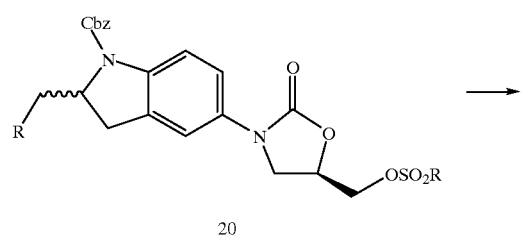
20
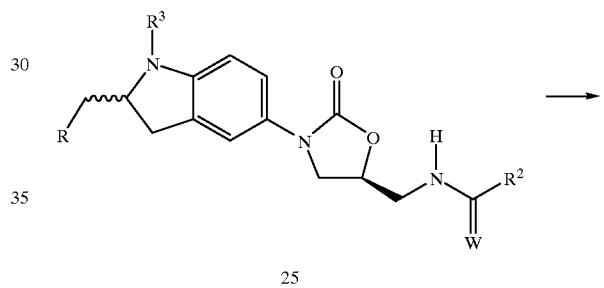
25
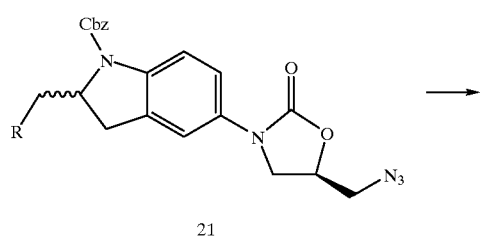
21
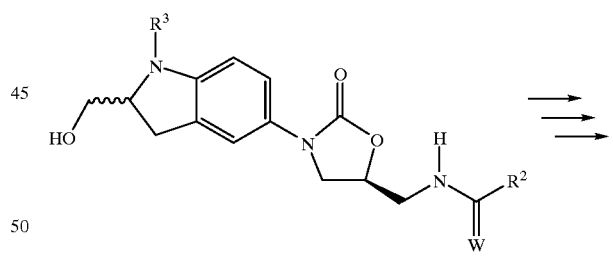
26
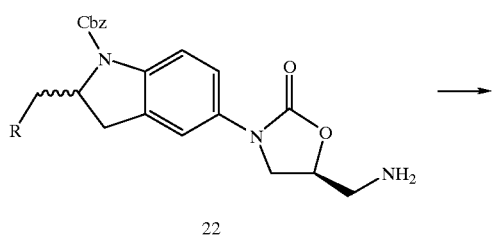
22
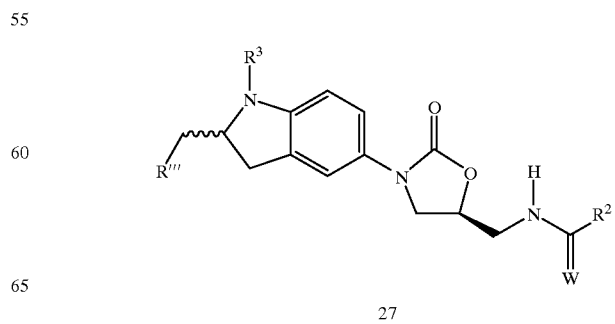
27

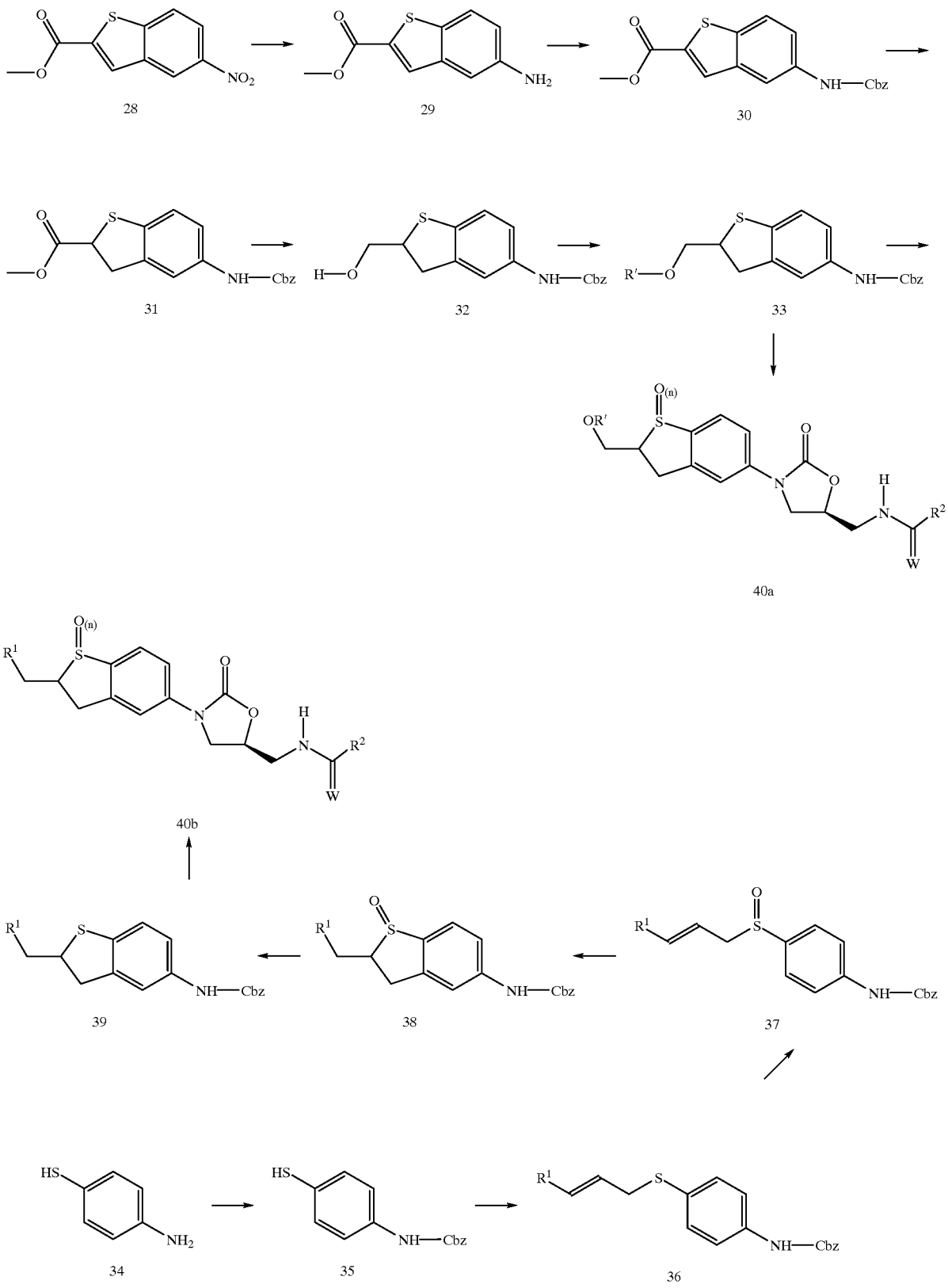
Chart IV

Chart V
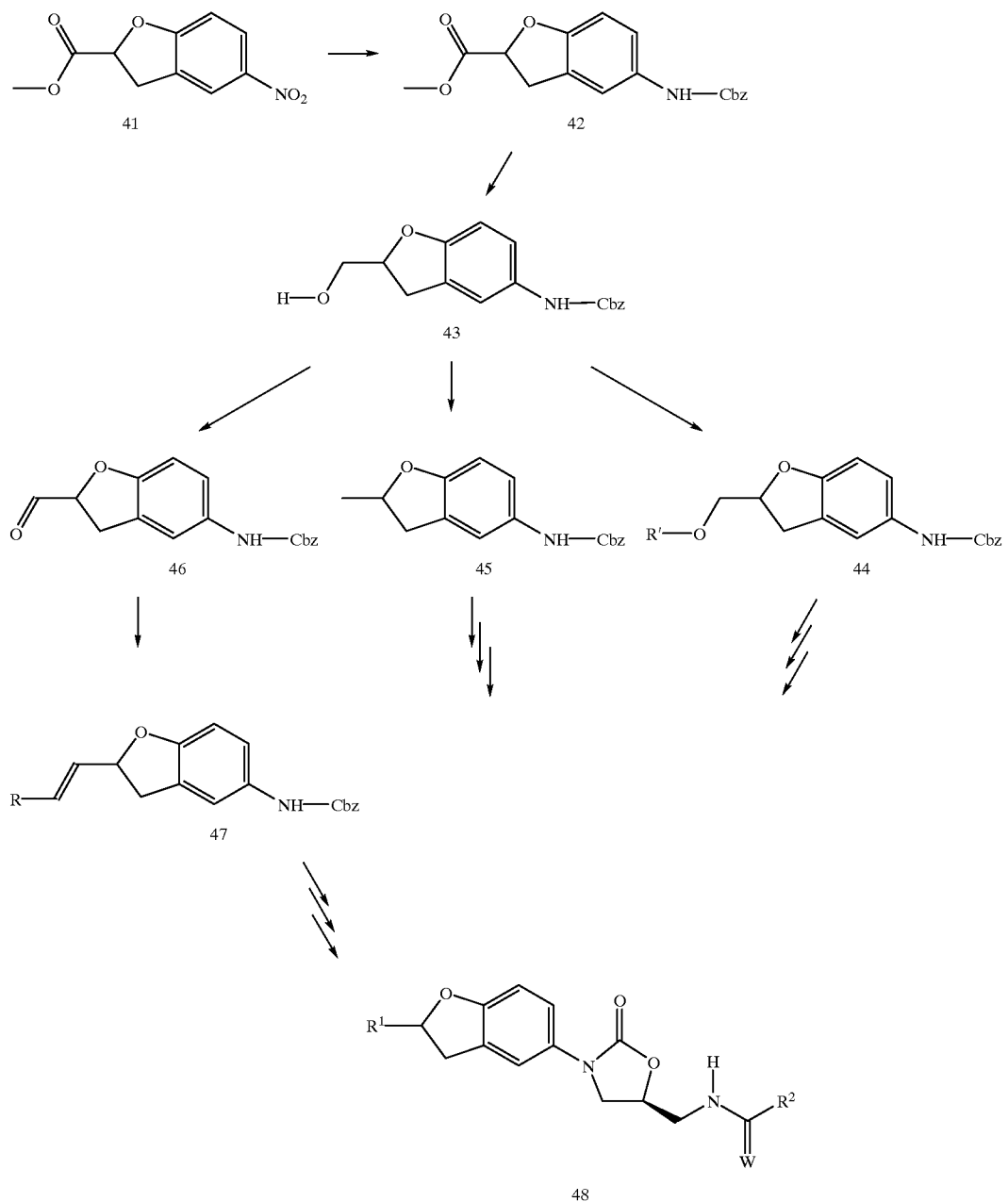
CHART VI
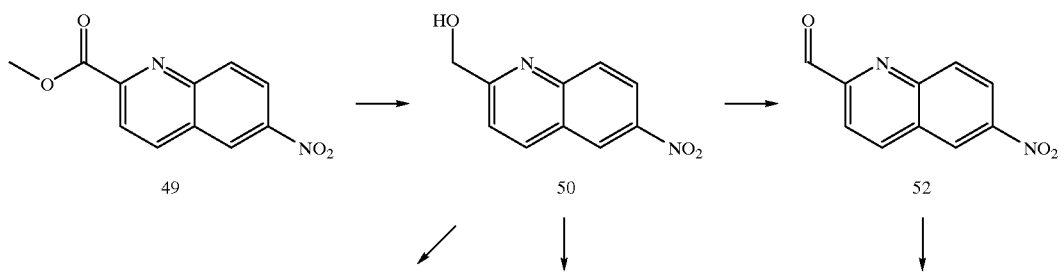

-continued
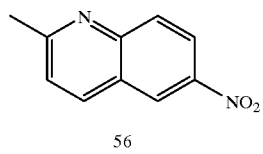
56
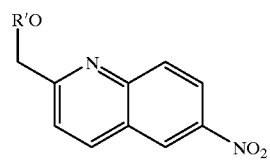
51
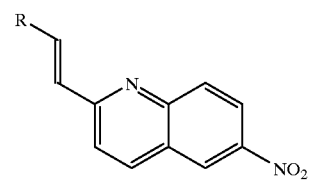
53
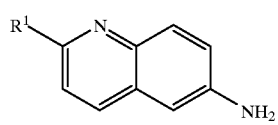
54
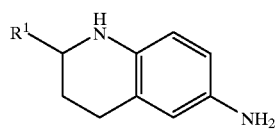
55
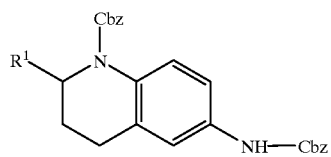
57
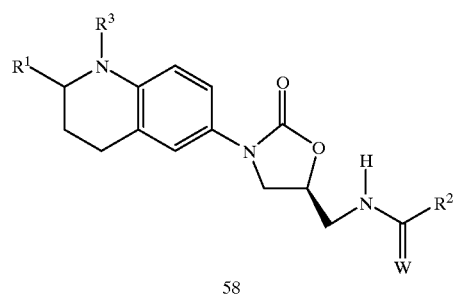
58

CHART VII
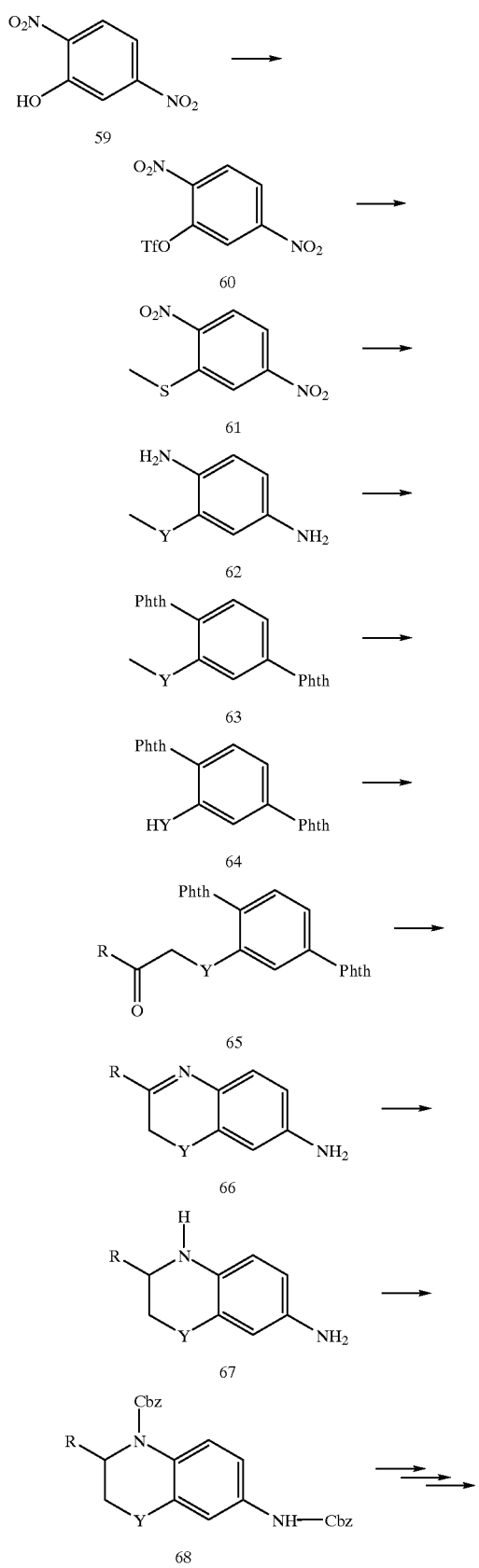
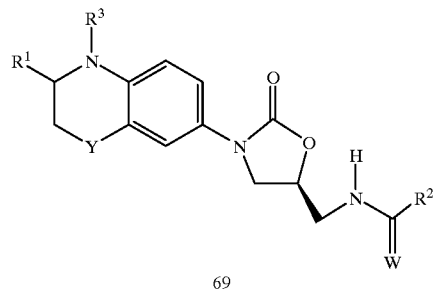
CHART VIII
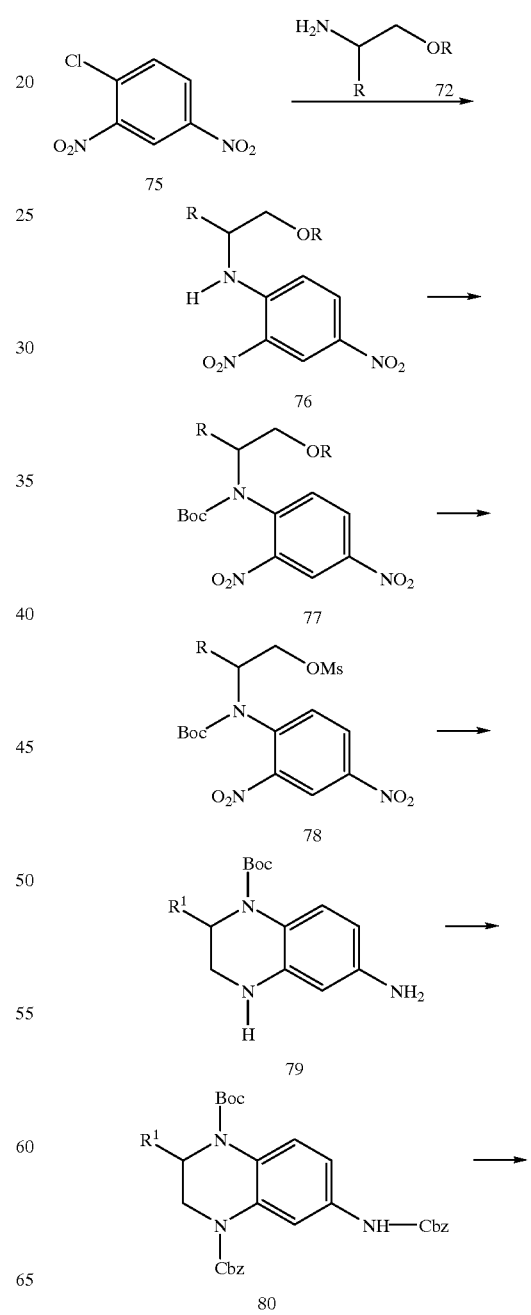

51
-continued
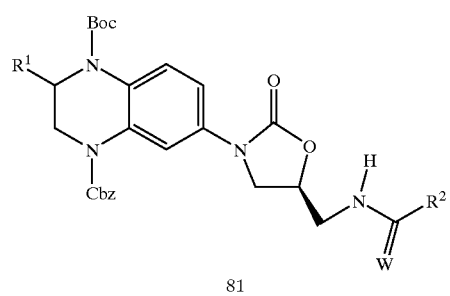
81
52
-continued
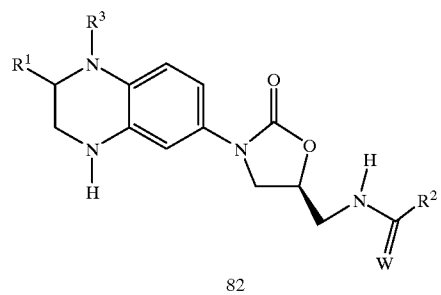
82
CHART IX
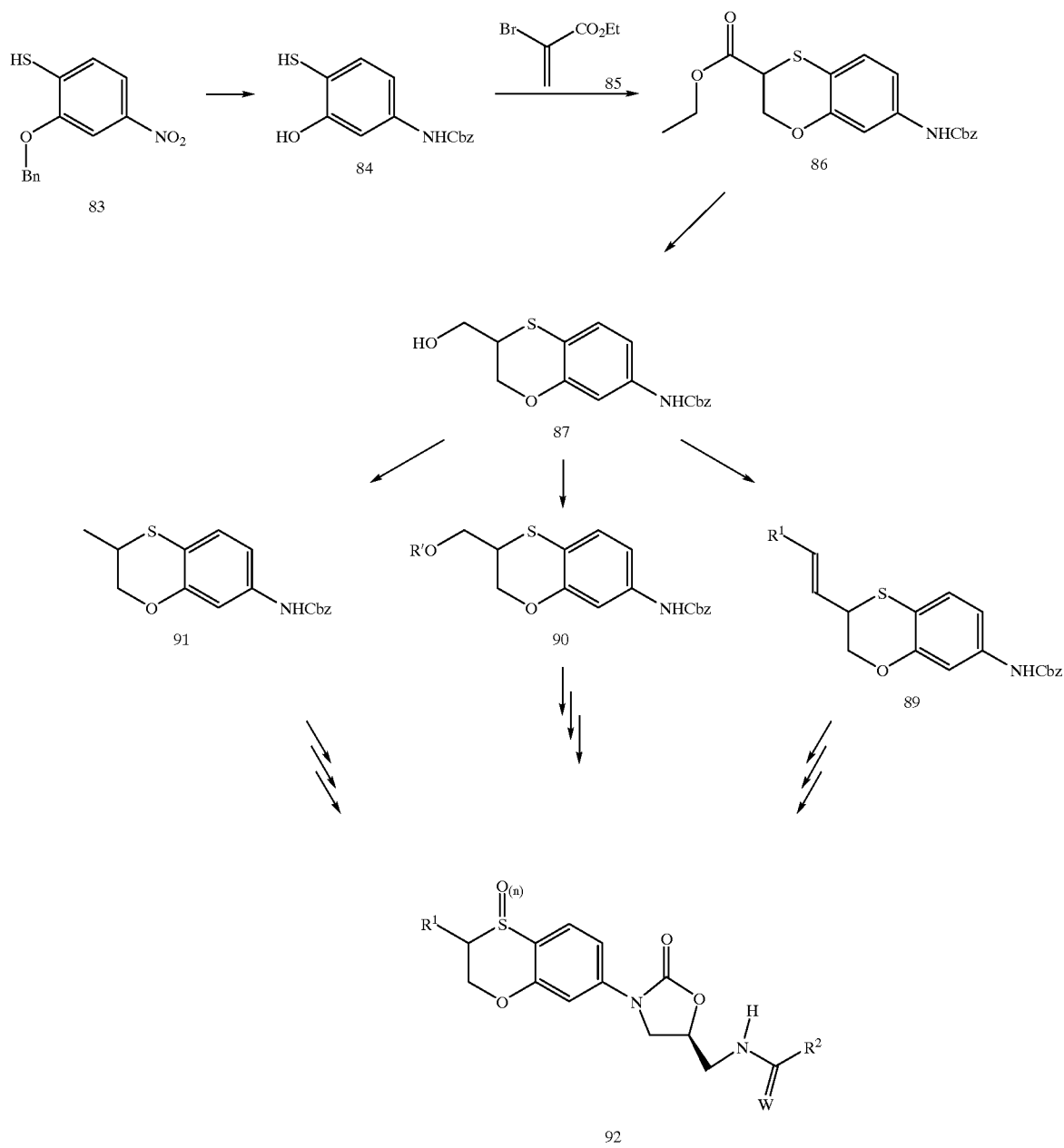

CHART X
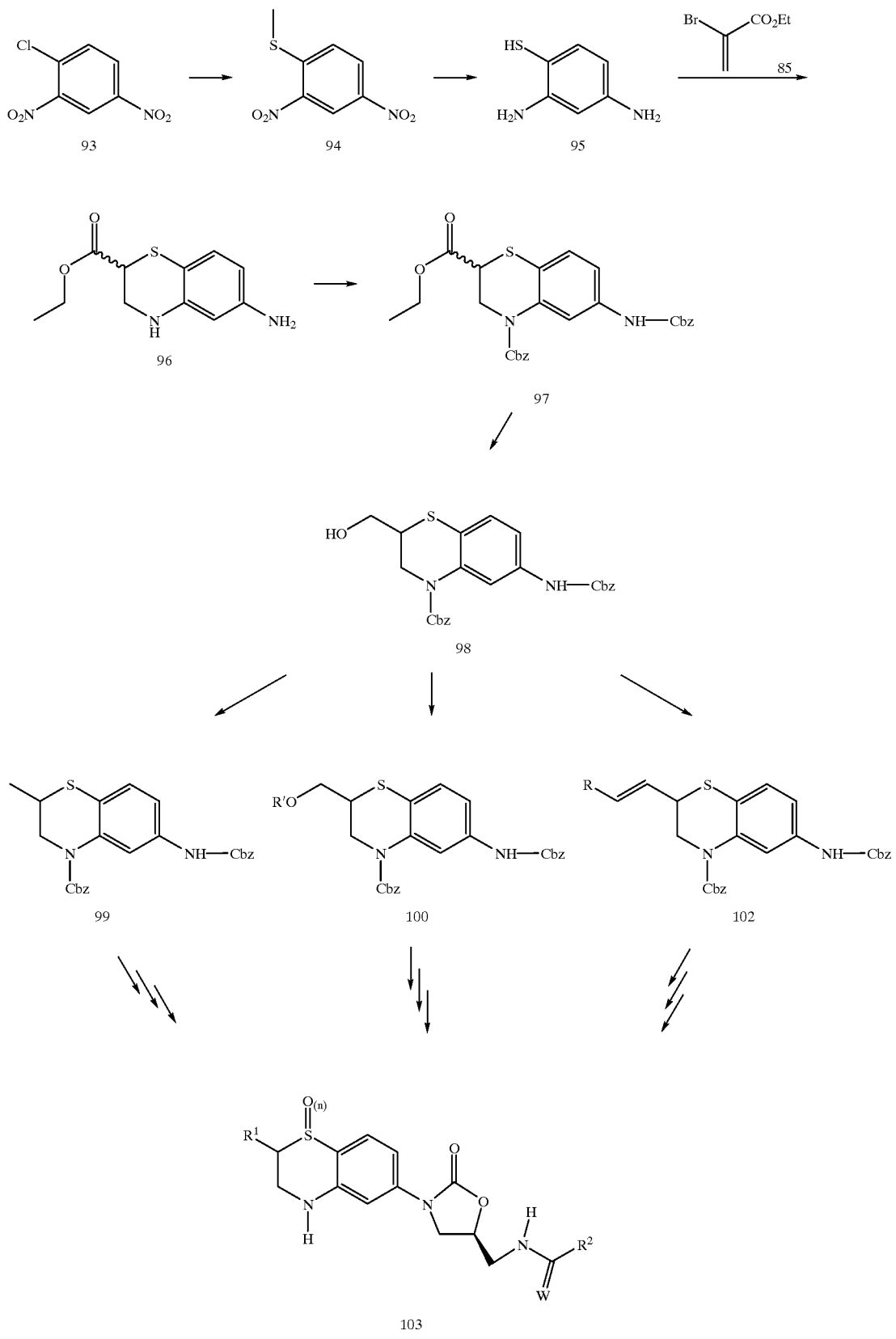

CHART XI
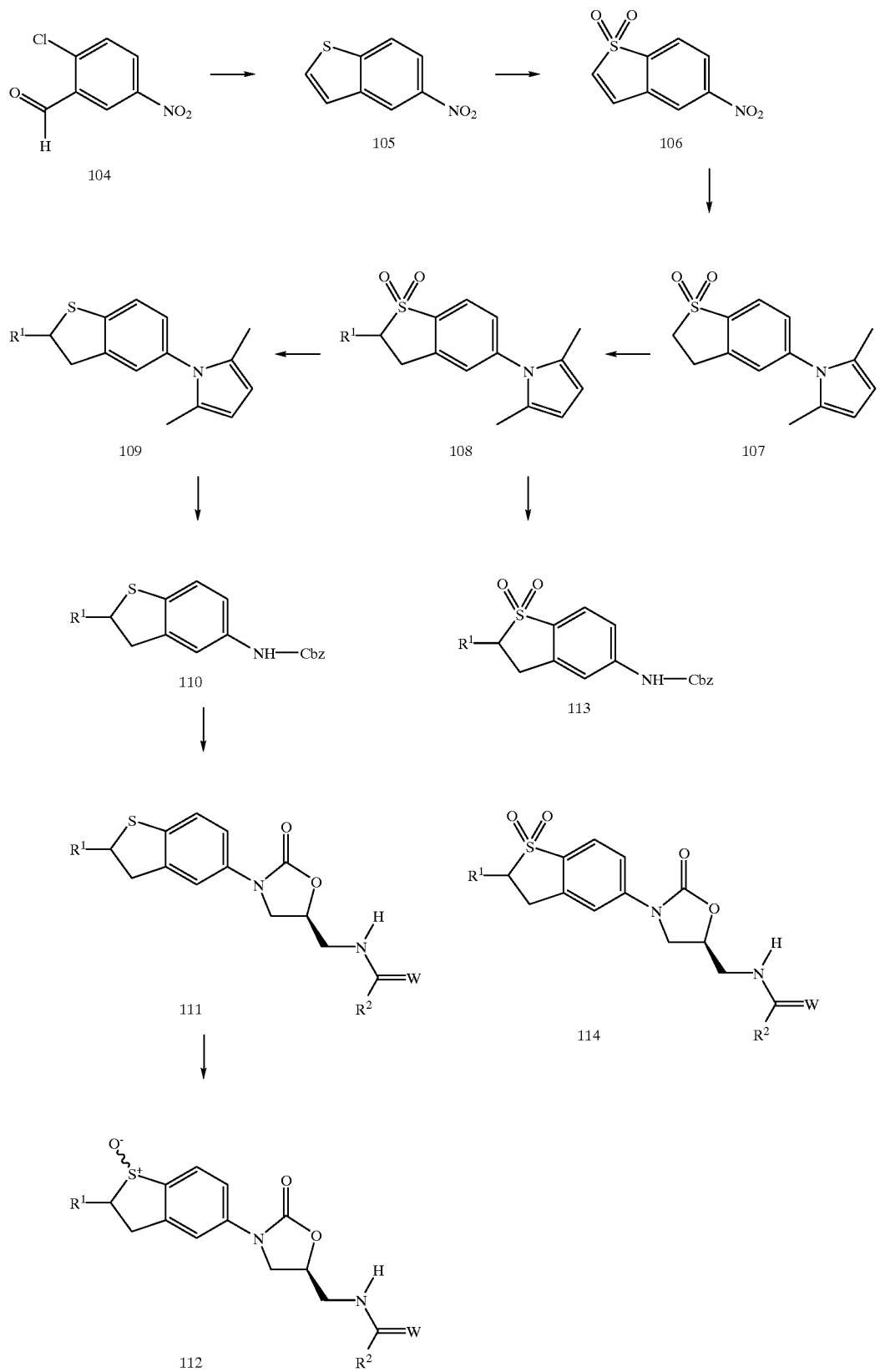

We claim:
1. A compound of formula I

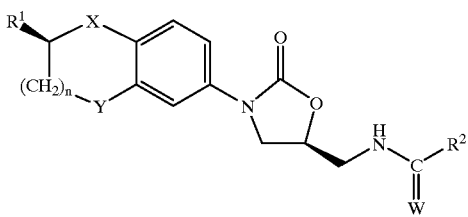

or a pharmaceutically acceptable salt thereof wherein:
W is
  a) O, or
  b) S;
X is
  a) —S(=O)$_m$—, or
  b) —NR$^3$—;
Y is
  a) —O—,
  b) —NH—,
  c) —CH$_2$—, or
  d) —S(=O)$_m$—;
R$^1$ is C$_{1-4}$ alkyl, optionally substituted with 1–3 R$^5$;
R$^2$ is
  a) H,
  b) C$_{1-6}$ alkyl, optionally substituted with 1–3 halo;
  c) cyclopropyl,
  d) —OC$_{1-4}$ alkyl,
  e) —NH$_2$,
  f) —NHC$_{1-6}$ alkyl, or
  g) —N(C$_{1-6}$ alkyl)$_2$;
R$^3$ is
  a) C$_{1-8}$ alkyl, optionally substituted with 1–3 halo, CN, NO$_2$, OH, SH or NH$_2$,
  b) —C(=O)R$^4$, or
  c) —C(=S)NHC$_{1-4}$ alkyl;
R$^4$ is
  a) H,
  b) C$_{1-6}$ alkyl, optionally substituted with OH, C$_{1-4}$ alkoxy, NH$_2$, SH or halo, or
  c) —CH$_2$OC(=O)C$_{1-4}$ alkyl;
R$^5$ is
  j) halo,
  k) —CN,
  l) —OH,
  m) —SH,
  n) —NH$_2$,
  o) —OR$^6$,
  p) —NHR$^6$,
  q) —N(R$^6$)$_2$, or
  r) —S(=O)$_m$R$^6$;
R$^6$ is
  g) C$_{1-6}$ alkyl,
  h) —C(=O)C$_{1-4}$ alkyl,
  i) —C(=O)OC$_{1-4}$ alkyl,
  j) —C(=O)NH$_2$,
  k) —C(=O)NHC$_{1-4}$ alkyl, or
  l) —SO$_2$C$_{1-4}$ alkyl;
m is 0, 1, or 2;
n is 0 or 1;
with the proviso that were n is 0, Y is —CH$_2$—.

2. A compound of claim 1 wherein R$^1$ is methyl; X is —NR$^3$—; R$^3$ is formyl or acetyl; R$^2$ is methyl or ethyl; Y is —CH$_2$—; W is sulfur; and n is 0 or 1.

3. A compound of claim 1 wherein R$^1$ is methyl; X is —NR$^3$—; R$^3$ is formyl or acetyl; R$^2$ is methyl or ethyl; Y is —O—; W is sulfur; and n is 1.

4. A compound of claim 1 wherein X is —NR$^3$—; R$^3$ is 2-fluoroethyl, glycolyl, formyl, methoxyacetyl, oxoethylacetate, acetyl, or methylaminocarbothioyl, R$^1$, R$^2$, n, W and Y are the same as in claim 1.

5. A compound of claim 1 wherein X is —NR$^3$—; R$^3$ is is formyl or acetyl; R$^1$, R$^2$, n, W and Y are the game as in claim 1.

6. A compound of claim 1 wherein X is —NR$^3$—; R$^3$ is as defined in claim 1; R$^1$, R$^2$, n, W and Y are the same as in claim 1.

7. A compound of claim 1 wherein Y is —CH$_2$—; R$^1$, R$^2$, n, W and X are the same as in claim 1.

8. A compound of claim 1 which is a) N-({(5S)-3-[(2R)-1-(2-fluoroethyl)-2-methyl-2,3-dihydro-1H-indol-5-yl]-2-oxo-1,3-oxazolidin-5-yl}methyl)acetamide;
b) N-{[(5S)-3-((2R)-1-glycoloyl-2-methyl-2,3-dihydro-1H-indol-5-yl)-2-oxo-1,3-oxazolidin-5-yl]methyl}acetamide;
c) N-({(5S)-3-[(2R)-1-glycoloyl-2-methyl-2,3-dihydro-1H-indol-5-yl]-2-oxo-1,3-oxazolidin-5-yl}methyl)acetamide;
d) N-({(5S)-3-[(2R)-1-formyl-2-methyl-2,3-dihydro-1H-indol-5-yl]-2-oxo-1,3-oxazolidin-5-yl}methyl)acetamide;
e) N-({(5S)-3-[(2R)-1-formyl-2-methyl-2,3-dihydro-1H-indol-5-yl]-2-oxo-1,3-oxazolidin-5-yl}methyl)propanamide;
f) N-({(5S)-3-[(2R)-1-formyl-2-methyl-2,3-dihydro-1H-indol-5-yl]-2-oxo-1,3-oxazolidin-5-yl}methyl)ethanethioamide;
g) N-({(5S)-3-[(2R)-1-(2-methoxyacetyl)-2-methyl-2,3-dihydro-1H-indol-5-yl]-2-oxo-1,3-oxazolidin-5-yl}methyl)acetamide;
h) 2-((2R)-5-{(5S)-5-[(acetylamino)methyl]-2-oxo-1,3-oxazolidin-3-yl}-2-methyl-2,3-dihydro-1H-indol-1-yl)-2-oxoethyl acetate;
i) N-({(5S)-3-[(2R)-1-acetyl-2-methyl-2,3-dihydro-1H-indol-5-yl]-2-oxo-1,3-oxazolidin-5-yl}methyl)acetamide;
j) N-[((5S)-3-{(2R)-2-methyl-1-[(methylamino)carbothioyl]-2,3-dihydro-1H-indol-5-yl}-2-oxo-1,3-oxazolidin-5-yl)methyl]acetamide;
k) 2-((2R)-5-{(5S)-5-[(ethanethioylamino)methyl]-2-oxo-1,3-oxazolidin-3-yl}-2-methyl-2,3-dihydro-1H-indol-1-yl)-2-oxoethyl acetate;
l) N-({(5S)-3-[(2R)-1-glycoloyl-2-methyl-2,3-dihydro-1H-indol-5-yl]-2-oxo-1,3-oxazolidin-5-yl}methyl)ethanethioamide;
m) N-{[(5S)-3-[(2R)-1-formyl-2-methyl-1,2,3,4-tetrahydro-6-quinolinyl]-2-oxo-1,3-oxazolidin-5-yl]methyl}acetamide;
n) N-{[(5S)-3-[(2R)-1-glycoloyl-2-methyl-1,2,3,4-tetrahydro-6-quinolinyl]-2-oxo-1,3-oxazolidin-5-yl]methyl}acetamide;
o) N-({(5S)-3-[(2R)-1-formyl-2-methyl-1,2,3,4-tetrahydro-6-quinolinyl]-2-oxo-1,3-oxazolidin-5-yl}methyl)acetamide;
p) N-({(5S)-3-[(2R)-1-formyl-2-methyl-1,2,3,4-tetrahydro-6-quinolinyl]-2-oxo-1,3-oxazolidin-5-yl}methyl)ethanethioamide;
q) N-{[(5S)-3-[(3R)-4-formyl-3-methyl-3,4-dihydro-2H-1,4-benzoxazin-7-yl]-2-oxo-1,3-oxazolidin-5-yl]methyl}acetamide;
r) N-({(5S)-3-[(3R)-4-formyl-3-methyl-3,4-dihydro-2H-1,4-benzoxazin-7-yl]-2-oxo-1,3-oxazolidin-5-yl}methyl)ethanethioamide;

s) N-({(5S)-3-[(2R)-2-(fluoromethyl)-1-formyl-2,3-dihydro-1H-indol-5-yl]-2-oxo-2-1,3-oxazolidin-5-yl}methyl)acetamide;
t) N-{[(5R)-3-(2(+)-methyl-2,3-dihydro-1-benzothien-5-yl)-2-oxo-1,3-oxazolidin-5-yl]methyl}acetamide; or
u) N-[[(5S)-3-[2-(1,1-dimethylethyl)-1-formyl-2,3-dihydro-1H-indol-5-yl]-2-oxo-5-oxazolidinyl]methyl] ethanethioamide.

9. A compound of claim 1 which is a) N-({(5S)-3-[(2R)-1-formyl-2-methyl-2,3-dihydro-1H-indol-5-yl]-2-oxo-1,3-oxazolidin-5-yl}methyl) ethanethioamide;
b) N-({(5S)-3-[(2R)-1-(2-methoxyacetyl)-2-methyl-2,3-dihydro-1H-indol-5-yl]-2-oxo-1,3-oxazolidin-5-yl}methyl)acetamide;
c) 2-((2R)-5-{(5S)-5-[(acetylamino)methyl]-2-oxo-1,3-oxazolidin-3-yl}-2-methyl-2,3-dihydro-1H-indol-1-yl)-2-oxoethyl acetate;
d) N-({(5S)-3-[(2R)-1-acetyl-2-methyl-2,3-dihydro-1H-indol-5-yl]-2-oxo-1,3-oxazolidin-5-yl}methyl)acetamide;
e) N-[((5S)-3-{(2R)-2-methyl-1-[(methylamino)carbothioyl]-2,3-dihydro-1H-indol-5-yl}-2-oxo-1,3-oxazolidin-5-yl)methyl]acetamide;
f) 2-((2R)-5-{(5S)-5-[(ethanethioylamino)methyl]-2-oxo-1,3-oxazolidin-3-yl}-2-methyl-2,3-dihydro-1H-indol-1-yl)-2-oxoethyl acetate;
g) N-({(5S)-3-[(2R)-1-glycoloyl-2-methyl-2,3-dihydro-1H-indol-5-yl]-2-oxo-1,3-oxazolidin-5-yl}methyl) ethanethioamide;
h) N-({(5S)-3-[(2R)-1-formyl-2-methyl-1,2,3,4-tetrahydro-6-quinolinyl]-2-oxo-1,3-oxazolidin-5-yl}methyl) acetamide;
i) N-({(5S)-3-[(2R)-1-formyl-2-methyl-1,2,3,4-tetrahydro-6-quinolinyl]-2-oxo-1,3-oxazolidin-5-yl}methyl) ethanethioamide;
j) N-({(5S)-3-[(3R)-4-formyl-3-methyl-3,4-dihydro-2H-1,4-benzoxazin-7-yl]-2-oxo-1,3-oxazolidin-5-yl}methyl) acetamide;
k) N-({(5S)-3-[(3R)-4-formyl-3-methyl-3,4-dihydro-2H-1,4-benzoxazin-7-yl]-2-oxo-1,3-oxazolidin-5-yl}methyl) ethanethioamide; or
l) N-[[(5S)-3-[2-(1,1-dimethylethyl)-1-formyl-2,3-dihydro-1H-indol-5-yl]-2-oxo-5-oxazolidinyl]methyl] ethanethioamide.

10. A compound of claim 1 which is a) N-({(5S)-3-[(2R)-1-formyl-2-methyl-2,3-dihydro-1H-indol-5-yl]-2-oxo-1,3-oxazolidin-5-yl}methyl) ethanethioamide;
b) N-({(5S)-3-[(2R)-1-glycoloyl-2-methyl-2,3-dihydro-1H-indol-5-yl]-2-oxo-1,3-oxazolidin-5-yl}methyl) ethanethioamide;
c) N-({(5S)-3-[(2R)-1-formyl-2-methyl-1,2,3,4-tetrahydro-6-quinolinyl]-2-oxo-1,3-oxazolidin-5-yl}methyl) ethanethioamide; or
d) N-({(5S)-3-[(3R)-4-formyl-3-methyl-3,4-dihydro-2H-1,4-benzoxazin-7-yl]-2-oxo-1,3-oxazolidin-5-yl}methyl) ethanethioamide.

11. A method for treating microbial infections in patients comprising: administering to a human or warm blood animals in need thereof an effective amount of a compound of formula I as shown in claim 1.

12. The method of claim 11 wherein said compound of formula I is administered orally, parenterally, transdermally, or topically in a pharmaceutical composition.

13. The method of claim 11 wherein said compound is administered in an amount of from about 0.1 to about 100 mg/kg of body weight/day.

14. The method of claim 11 wherein said compound is administered in an amount of from about 1 to about 50 mg/kg of body weight/day.

15. A method for treating microbial infections of claim 11 wherein the infection is a skin infection.

16. A method for treating microbial infections of claim 11 wherein the infection is an eye infection.

17. A pharmaceutical composition comprising a compound of claim 1 and a pharmaceutically acceptable carrier.

18. A compound of formula I

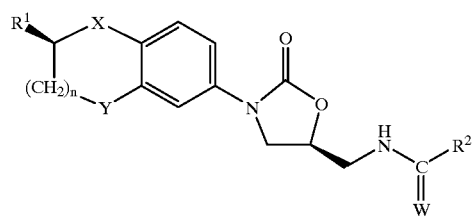

or a pharmaceutically acceptable salt thereof wherein:
W is
 a) S;
X is
 a) —S(=O)$_m$—, or
 b) —NR$^3$—;
Y is
 a) —O—,
 b) —NH—,
 c) —CH$_2$—, or
 d) —S(=O)$_m$—;
R$^1$ is C$_{1-4}$ alkyl, optionally substituted with 1–3 R$^5$;
R$^2$ is
 a) H,
 b) C$_{1-6}$ alkyl, optionally substituted with 1–3 halo;
 c) cyclopropyl,
 d) —OC$_{1-4}$ alkyl,
 e) —NH$_2$,
 f) —NHC$_{1-6}$ alkyl, or
 g) —N(C$_{1-6}$ alkyl)$_2$;
R$^3$ is
 a) C$_{1-8}$ alkyl, optionally substituted with 1–3 halo, CN, NO$_2$, OH, SH or NH$_2$,
 b) —C(=O)R$^4$, or
 c) —C(=S)NHC$_{1-4}$ alkyl;
R$^4$ is
 a) H,
 b) C$_{1-6}$ alkyl, optionally substituted with OH, C$_{1-4}$ alkoxy, NH$_2$, SH or halo, or
 c) —CH$_2$OC(=O)C$_{1-4}$ alkyl;
R$^5$ is
 a) halo,
 b) —CN,
 c) —OH,
 d) —SH,
 e) —NH$_2$,
 f) —OR$^6$,
 g) —NHR$^6$,
 h) —N(R$^6$)$_2$, or
 i) —S(=O)$_m$R$^6$;
R$^6$ is
 a) C$_{1-6}$ alkyl,
 b) —C(=O)C$_{1-4}$ alkyl,
 c) —C(=O)OC$_{1-4}$ alkyl, d) —C(=O)NH$_2$,
e) —C(=O)NHC$_{1-4}$ alkyl, or
f) —SO$_2$C$_{1-4}$ alkyl;

m is 0, 1 or 2;
n is 0 or 1;
with the proviso that where n is 0, Y is —CH$_2$—.

19. A compound of formula I

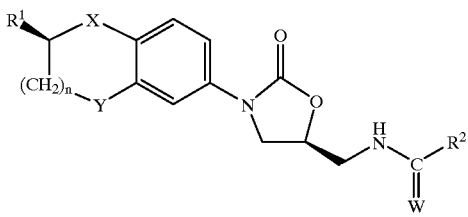

or a pharmaceutically acceptable salt thereof wherein:
W is
  a) O, or
  b) S;
X is
  a) —S(=O)$_m$—, or
  b) —NR$^3$—;
Y is
  a) —O—;
R$^1$ is C$_{1-4}$ alkyl, optionally substituted with 1–3 R$^5$;
R$^2$ is
  a) H,
  b) C$_{1-6}$ alkyl, optionally substituted with 1–3 halo
  c) cyclopropyl,
  d) —OC$_{1-4}$ alkyl,
  e) —NH$_2$,
  f) —NHC$_{1-6}$ alkyl, or
  g) —N(C$_{1-6}$ alkyl)$_2$;
R$^3$ is
  a) C$_{1-8}$ alkyl, optionally substituted with 1–3 halo, CN, NO$_2$, OH, SH or NH$_2$,
  b) —C(=O)R$^4$, or
  c) —C(=S)NHC$_{1-4}$ alkyl;
R$^4$ is
  a) H,
  b) C$_{1-6}$ alkyl, optionally substituted with OH, C$_{1-4}$ alkoxy, NH$_2$, SH or halo, or
  c) —CH$_2$OC(=O)C$_{1-4}$ alkyl;
R$^5$ is
  a) halo,
  b) —CN,
  c) —OH,
  d) —SH,
  e) —NH$_2$,
  f) —OR$^6$,
  g) —NHR$^6$,
  h) —N(R$^6$)$_2$, or
  i) —S(=O)$_m$R$^6$;
R$^6$ is
  a) C$_{1-6}$ alkyl,
  b) —C(=O)C$_{1-4}$ alkyl,
  c) —C(=O)OC$_{1-4}$ alkyl,
  d) —C(=O)NH$_2$,
  e) —C(=O)NHC$_{1-4}$ alkyl, or
  f) —SO$_2$C$_{1-4}$ alkyl;

m is 0, 1 or 2; and
n is 0 or 1.

20. A compound of formula I

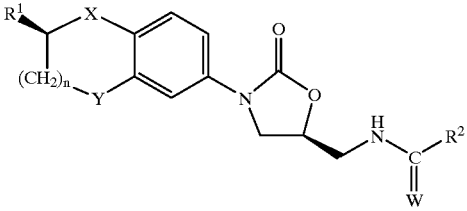

or a pharmaceutically acceptable salt thereof wherein:
W is
  a) O, or
  b) S;
X is
  a) —S(=O)$_m$—, or
  b) —NR$^3$—;
Y is
  a) —O—
  b) —NH—,
  c) —CH$_2$—, or
  d) —S(=O)$_m$—;
R$^1$ is C$_{1-4}$ alkyl, optionally substituted with 1–3 R$^5$;
R$^2$ is
  a) H,
  b) C$_{1-6}$ alkyl, optionally substituted with 1–3 halo;
  c) cyclopropyl,
  d) —OC$_{1-4}$ alkyl,
  e) —NH$_2$,
  f) —NHC$_{1-6}$ alkyl, or
  g) —N(C$_{1-6}$ alkyl)$_2$;
R$^3$ is
  a) C$_{1-8}$ alkyl, optionally substituted with 1–3 halo, CN, NO$_2$, OH, SH or NH$_2$,
  b) —C(=O)R$^4$, or
  c) —C(=S)NHC$_{1-4}$ alkyl;
R$^4$ is
  a) H,
  b) C$_{1-6}$ alkyl, optionally substituted with OH, C$_{1-4}$ alkoxy, NH$_2$, SH or halo, or
  c) —CH$_2$OC(=O)C$_{1-4}$ alkyl;
R$^5$ is
  a) halo,
  b) —CN,
  c) —OH,
  d) —SH,
  e) —NH$_2$,
  f) —OR$^6$,
  g) —NHR$^6$,
  h) —N(R$^6$)$_2$, or
  i) —S(=O)$_m$R$^6$;
R$^6$ is
  a) C$_{1-6}$ alkyl,
  b) —C(=O)C$_{1-4}$ alkyl,
  c) —C(=O)OC$_{1-4}$ alkyl,
  d) —C(=O)NH$_2$,
  e) —C(=O)NHC$_{1-4}$ alkyl, or
  f) —SO$_2$C$_{1-4}$ alkyl; m is 0, 1 or 2; and n is 1.

21. A compound having the formula N-({(5S)-3-[(2R)-1-formyl-2-methyl-1,2,3,4-tetrahydro-6-quinolinyl]-2-oxo-1,3-oxazolidin-5-yl}methyl)ethanethioamide.

* * * * *